(12) United States Patent
Smith et al.

(10) Patent No.: US 11,911,305 B2
(45) Date of Patent: Feb. 27, 2024

(54) STENT DEPLOYMENT SYSTEM

(71) Applicant: BOSTON SCIENTIFIC SCIMED, INC., Maple Grove, MN (US)

(72) Inventors: Amanda Lynn Smith, Boston, MA (US); John T. Favreau, Spencer, MA (US); Jacqueline Nicole Magaha, Taneytown, MD (US); Jennifer Whelehan, Cortlandt Manor, NY (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 404 days.

(21) Appl. No.: 17/127,047

(22) Filed: Dec. 18, 2020

(65) Prior Publication Data
US 2021/0228389 A1 Jul. 29, 2021

Related U.S. Application Data

(60) Provisional application No. 62/966,282, filed on Jan. 27, 2020.

(51) Int. Cl.
*A61F 2/97* (2013.01)
*A61F 2/966* (2013.01)
*A61F 2/962* (2013.01)

(52) U.S. Cl.
CPC ............... *A61F 2/97* (2013.01); *A61F 2/966* (2013.01); *A61F 2002/9623* (2020.05); *A61F 2250/0071* (2013.01)

(58) Field of Classification Search
CPC .... A61F 2/97; A61F 2/966; A61F 2002/9623; A61F 2002/9665
See application file for complete search history.

(56) References Cited

U.S. PATENT DOCUMENTS

| | | |
|---|---|---|
| 5,405,378 A | 4/1995 | Strecker |
| 5,647,857 A | 7/1997 | Anderson et al. |
| 5,824,041 A | 10/1998 | Lenker et al. |
| 5,941,855 A | 8/1999 | Picha et al. |
| 5,948,191 A | 9/1999 | Solovay |
| 6,352,553 B1 | 3/2002 | van der Burg et al. |
| 6,352,561 B1 | 3/2002 | Leopold et al. |
| 6,878,153 B2 | 4/2005 | Linder et al. |
| 6,939,368 B2 | 9/2005 | Simso |
| 6,951,570 B2 | 10/2005 | Linder et al. |
| 6,962,598 B2 | 11/2005 | Linder et al. |
| 6,997,939 B2 | 2/2006 | Linder et al. |
| 7,285,130 B2 | 10/2007 | Austin |
| 7,678,068 B2 | 3/2010 | Levine et al. |

(Continued)

FOREIGN PATENT DOCUMENTS

JP        2014504904 A        2/2014

OTHER PUBLICATIONS

International Search Report and Written Opinion dated May 28, 2021 for International Application No. PCT/US2020/066061.

*Primary Examiner* — William H Matthews
(74) *Attorney, Agent, or Firm* — Seager, Tufte & Wickhem, LLP

(57) ABSTRACT

A delivery system for delivering a stent to a body lumen. The delivery system includes a tubular member having an expandable stent disposed about the outer surface of the inner tubular member. The stent is maintained in a radially compressed configuration with a removable sheath. The sheath can be released using a variety of techniques.

20 Claims, 20 Drawing Sheets

(56) References Cited

U.S. PATENT DOCUMENTS

| | | |
|---|---|---|
| 8,545,544 B2 | 10/2013 | Spenser et al. |
| 8,579,957 B2 | 11/2013 | Linder et al. |
| 8,834,550 B2 | 9/2014 | Leanna et al. |
| 8,915,951 B2 | 12/2014 | Weber |
| 8,961,582 B2 | 2/2015 | Holm et al. |
| 9,211,206 B2 | 12/2015 | Pryor |
| 9,314,356 B2 | 4/2016 | McHugo et al. |
| 9,402,755 B2 | 8/2016 | Norris et al. |
| 9,474,640 B2 | 10/2016 | Johnson |
| 9,675,487 B2 | 6/2017 | Brown |
| 2002/0004676 A1 | 1/2002 | Wallace et al. |
| 2002/0007208 A1 | 1/2002 | Strecker |
| 2004/0024441 A1 | 2/2004 | Bertolino et al. |
| 2004/0064179 A1 | 4/2004 | Linder et al. |
| 2004/0143315 A1 | 7/2004 | Bruun et al. |
| 2004/0230285 A1 | 11/2004 | Gifford et al. |
| 2004/0267347 A1 | 12/2004 | Cervantes |
| 2005/0143773 A1 | 6/2005 | Abrams et al. |
| 2008/0255580 A1* | 10/2008 | Hoffman .............. A61F 2/97 606/108 |
| 2009/0204196 A1 | 8/2009 | Weber |
| 2010/0211156 A1 | 8/2010 | Linder et al. |
| 2010/0331960 A1 | 12/2010 | Clerc et al. |
| 2011/0077730 A1 | 3/2011 | Fenster |
| 2012/0172887 A1 | 7/2012 | Hatfield |
| 2016/0045351 A1 | 2/2016 | Dorn et al. |
| 2016/0317336 A1 | 11/2016 | Norris et al. |
| 2018/0360589 A1 | 12/2018 | Nolan et al. |

\* cited by examiner

STENT DEPLOYMENT SYSTEM

CROSS REFERENCE TO RELATED APPLICATIONS

The present application claims the benefit of and priority to U.S. Provisional patent Application Ser. No. 62/966,282, filed on Jan. 27, 2020, the disclosure of which is incorporated herein by reference.

TECHNICAL FIELD

The present disclosure relates generally to methods and apparatuses for deployment of stents. More particularly, the disclosure relates to different configurations and methods of deployment systems for deploy a high friction stent.

BACKGROUND

Implantable stents are devices that are placed in a body structure, such as a blood vessel, esophagus, trachea, biliary tract, colon, intestine, stomach or body cavity, to provide support and to maintain the structure open. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

SUMMARY

This disclosure is directed to several alternative designs, materials, and methods of manufacturing medical device structures and assemblies for delivery of stents within the body.

In a first example, a delivery system for delivering a stent to a body lumen may comprise an outer tubular member defining a lumen and having a proximal end region and a distal end region, a cutting element coupled to an inner surface of the outer tubular member adjacent to the distal end region thereof, the cutting element extending radially inward from the inner surface, an inner tubular member defining a lumen and having a proximal end region and a distal end region, the inner tubular member slidably disposed within the lumen of the outer tubular member, an expandable stent disposed about the outer surface of the inner tubular member adjacent the distal end region of the inner tubular member, and a sheath releasably disposed over the expandable stent and configured to maintain the expandable stent in a radially collapsed configuration. The cutting element may be configured to cut the sheath upon proximal retraction of the outer tubular member while remaining radially spaced from the expandable stent.

Alternatively or additionally to any of the examples above, in another example, the cutting element may comprise a blade.

Alternatively or additionally to any of the examples above, in another example, the cutting element may comprise a saw tooth blade.

Alternatively or additionally to any of the examples above, in another example, the cutting element may comprise a pair of blades secured together to form a V shaped cutting surface.

Alternatively or additionally to any of the examples above, in another example, the cutting element may comprise two or more cutting elements uniformly positioned about a circumference of the inner surface of the outer tubular member.

Alternatively or additionally to any of the examples above, in another example, the cutting element may comprise two or more cutting elements eccentrically positioned about a circumference of the inner surface of the outer tubular member.

Alternatively or additionally to any of the examples above, in another example, the inner diameter of the outer tubular member may be greater than an outer diameter of the sheath.

Alternatively or additionally to any of the examples above, in another example, the sheath may comprise a plurality of perforations.

Alternatively or additionally to any of the examples above, in another example, the plurality of perforations may be radially aligned with the cutting element.

Alternatively or additionally to any of the examples above, in another example, upon proximal retraction of the outer tubular member, the sheath may be released from the stent.

Alternatively or additionally to any of the examples above, in another example, after the sheath is cut through proximal retraction of the outer tubular member, the sheath may be configured to be removable.

In another example, a delivery system for delivering a stent to a body lumen may comprise a tubular member defining a lumen and having a proximal end region and a distal end region, an expandable stent disposed about the outer surface of the inner tubular member adjacent the distal end region of the inner tubular member, a sheath releasably disposed over the expandable stent and configured to maintain the expandable stent in a radially collapsed configuration, and a release tab extending from a proximal end adjacent to a proximal end of the sheath to a distal end adjacent to a distal end of the sheath. The release tab may be configured to breakdown under an electrical or a chemical stimulus.

Alternatively or additionally to any of the examples above, in another example, the delivery system may further comprise a pair of electrically conductive wires coupled to the release tab.

Alternatively or additionally to any of the examples above, in another example, the delivery system may further comprise one or more ports formed in the tubular member adjacent to the expandable stent.

Alternatively or additionally to any of the examples above, in another example, the release tabs may comprise a two or more release tabs spaced about a circumference of the sheath.

In another example, a delivery system for delivering a stent to a body lumen may comprise an outer tubular member defining a lumen and having a proximal end region and a distal end region, a cutting element coupled to an inner surface of the outer tubular member adjacent to the distal end region thereof, the cutting element extending radially inward from the inner surface, an inner tubular member defining a lumen and having a proximal end region and a distal end region, the inner tubular member slidably disposed within the lumen of the outer tubular member, an expandable stent disposed about the outer surface of the inner tubular member adjacent the distal end region of the inner tubular member, and a sheath releasably disposed over the expandable stent and configured to maintain the expandable stent in a radially collapsed configuration. The cutting element may be configured to cut the sheath upon proximal retraction of the outer tubular member while remaining radially spaced from the expandable stent.

Alternatively or additionally to any of the examples above, in another example, the cutting element may comprise a blade.

Alternatively or additionally to any of the examples above, in another example, the cutting element may comprise a saw tooth blade.

Alternatively or additionally to any of the examples above, in another example, the cutting element may comprise a pair of blades secured together to form a V shaped cutting surface.

Alternatively or additionally to any of the examples above, in another example, the cutting element may comprise two or more cutting elements uniformly positioned about a circumference of the inner surface of the outer tubular member.

Alternatively or additionally to any of the examples above, in another example, the cutting element may comprise two or more cutting elements eccentrically positioned about a circumference of the inner surface of the outer tubular member.

Alternatively or additionally to any of the examples above, in another example, the inner diameter of the outer tubular member may be greater than an outer diameter of the sheath.

Alternatively or additionally to any of the examples above, in another example, the sheath may comprise a plurality of perforations.

Alternatively or additionally to any of the examples above, in another example, the plurality of perforations may be radially aligned with the cutting element.

Alternatively or additionally to any of the examples above, in another example, upon proximal retraction of the outer tubular member, the sheath may be released from the stent.

Alternatively or additionally to any of the examples above, in another example, after the sheath is cut through proximal retraction of the outer tubular member, the sheath may be configured to be removable.

In another example, a delivery system for delivering a stent to a body lumen may comprise a tubular member defining a lumen and having a proximal end region and a distal end region, an expandable stent disposed about the outer surface of the inner tubular member adjacent the distal end region of the inner tubular member, a sheath releasably disposed over the expandable stent and configured to maintain the expandable stent in a radially collapsed configuration, and a release tab extending from a proximal end adjacent to a proximal end of the sheath to a distal end adjacent to a distal end of the sheath. The release tab may be configured to breakdown under an applied electrical stimulus to create a tear in the sheath and release a compressive force of the sheath on the expandable stent.

Alternatively or additionally to any of the examples above, in another example, the delivery system may further comprise a pair of electrically conductive wires coupled to the release tab.

Alternatively or additionally to any of the examples above, in another example, the release tabs may comprise a two or more release tabs spaced about a circumference of the sheath.

Alternatively or additionally to any of the examples above, in another example, the release tab may comprise a thin metal wire.

Alternatively or additionally to any of the examples above, in another example, the release tab may extend generally parallel to a longitudinal axis of the sheath.

In another example, a delivery system for delivering a stent to a body lumen may comprise a tubular member defining a lumen and having a proximal end region and a distal end region, an expandable stent disposed about the outer surface of the inner tubular member adjacent the distal end region of the inner tubular member, a sheath releasably disposed over the expandable stent and configured to maintain the expandable stent in a radially collapsed configuration, and a release tab extending from a proximal end adjacent to a proximal end of the sheath to a distal end adjacent to a distal end of the sheath. The release tab may be configured to breakdown under a chemical stimulus to create a tear in the sheath and release a compressive force of the sheath on the expandable stent.

Alternatively or additionally to any of the examples above, in another example, the delivery system may further comprise one or more ports formed in the tubular member adjacent to the expandable stent for expelling a flow of a fluid therethrough.

Alternatively or additionally to any of the examples above, in another example, the fluid may be an acid.

Alternatively or additionally to any of the examples above, in another example, the fluid may be saline.

The above summary of exemplary embodiments is not intended to describe each disclosed embodiment or every implementation of the present disclosure.

BRIEF DESCRIPTION OF THE DRAWINGS

The invention may be more completely understood in consideration of the following detailed description of various embodiments in connection with the accompanying drawings, in which.

Figure 1:
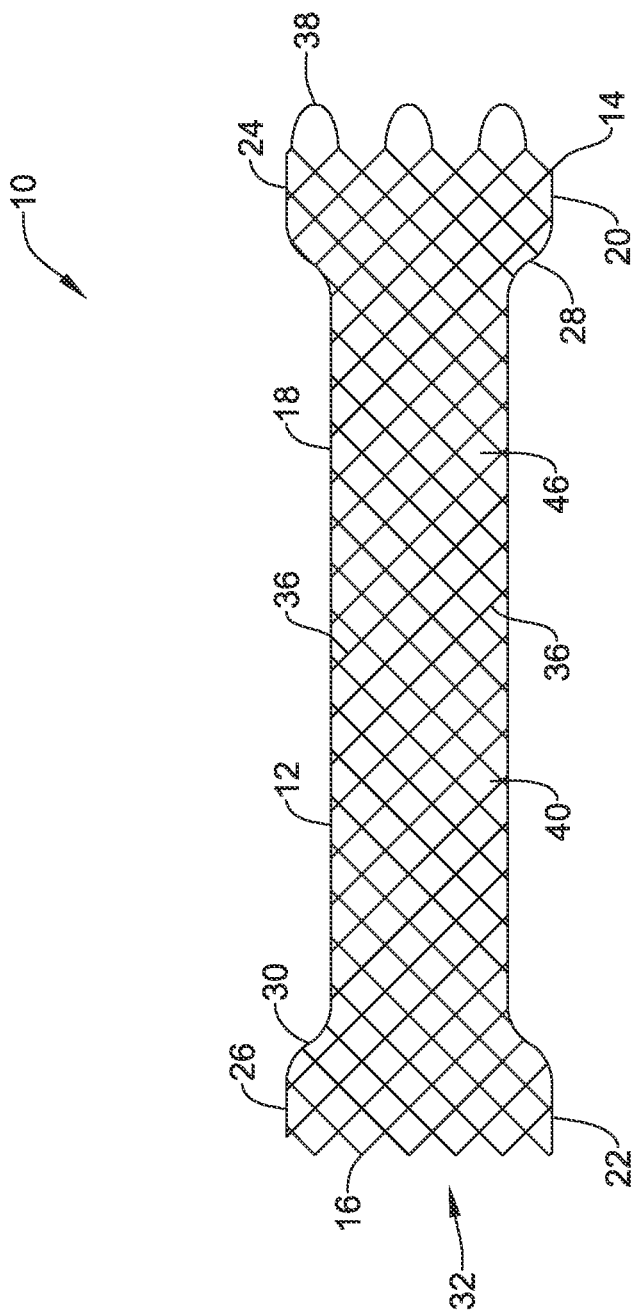
FIG. 1 is a side view of an illustrative stent.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may be indicative as including numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

Although some suitable dimensions, ranges, and/or values pertaining to various components, features and/or specifications are disclosed, one of the skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

For purposes of this disclosure, "proximal" refers to the end closer to the device operator during use, and "distal" refers to the end further from the device operator during use.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with one embodiment, it should be understood that such feature, structure, or characteristic may also be used connection with other embodiments whether or not explicitly described unless cleared stated to the contrary.

Anti-migration stent technologies (e.g., fully or partially coated stents, stents with mechanical fixations, stents with increased diameter and/or surface areas, etc.) as well as stents including active coatings (such as, but not limited to, drugs or anti-microbials) can increase the friction between the stent and a deployment system. This may lead to higher stent deployment forces and/or difficulties in deploying the stent. Deployment forces may also be driven by the radial force of a compressed stent. Higher deployment forces may result in a need to increase the size of a delivery device which is often contrary to market requirements. In some cases, delivery may be achieved by pulling an outer shaft off of the outside of the stent which may create a maximal friction force within the device. As an alternative to current stent deployment techniques, removing the outer sheath radially rather than axially from the stent may reduce surface area interaction between the outer sheath and the stent during deployment which decrease the force required for deployment.

FIG. 1 illustrates a side view of an illustrative endoluminal implant 10, such as, but not limited to, a stent. In some instances, the stent 10 may be formed from an elongated tubular member 12. While the stent 10 is described as generally tubular, it is contemplated that the stent 10 may take any cross-sectional shape desired. The stent 10 may have a first, or proximal end 14, a second, or distal end 16, and an intermediate region 18 disposed between the first end 14 and the second end 16. The stent 10 may include a lumen 32 extending from a first opening adjacent the first end 14 to a second opening adjacent to the second end 16 to allow for the passage of food, fluids, etc.

The stent 10 may be expandable from a first radially collapsed configuration (not explicitly shown) to a second radially expanded configuration. In some cases, the stent 10 may be deployed to a configuration between the collapsed configuration and a fully expanded configuration. The stent 10 may be structured to extend across a stricture and to apply a radially outward pressure to the stricture in a lumen to open the lumen and allow for the passage of foods, fluids, air, etc.

In some embodiments, the proximal end 14 of the stent 10 may include a plurality of loops 38. The loops 38 may be configured to receive a retrieval tether or suture (not explicitly shown) interwoven therethrough, or otherwise passing through one or more of the loops 38. The retrieval suture may be used to collapse and retrieve the stent 10, if so desired. For example, the retrieval suture may be pulled like a drawstring to radially collapse the proximal end 14 of the stent 10 to facilitate removal of the stent 10 from a body lumen.

The stent 10 may have a woven structure, fabricated from a number of filaments or struts 36 forming a tubular wall. In some embodiments, the stent 10 may be knitted or braided with a single filament or strut interwoven with itself and defining open cells 46 extending through the thickness of the tubular wall of the stent 10. In other embodiments, the stent 10 may be braided with several filaments or struts interwoven together and defining open cells 46 extending through the thickness of the tubular wall of the stent 10. Some exemplary stents including braided filaments include the WallFlex®, WALLSTENT®, and Polyflex® stents, made and distributed by Boston Scientific, Corporation. In another embodiment, the stent 10 may be knitted, such as the Ultraflex™ stents made by Boston Scientific, Corporation. In yet another embodiment, the stent 10 may be of a knotted type, such the Precision Colonic™ stents made by Boston Scientific, Corporation. In still another embodiment, the stent 10 may be a laser cut tubular member, such as the EPIC™ stents made by Boston Scientific, Corporation. A laser cut tubular member may have an open and/or closed cell geometry including one or more interconnected monolithic filaments or struts defining open cells 46 therebetween, with the open cells 46 extending through the thickness of the tubular wall. In some instances, an inner and/or outer surface of the tubular wall of the stent 10 may be entirely, substantially, or partially, covered with a polymeric covering or coating 40, as will be described in more detail herein. The covering or coating 40 may extend across and/or occlude one or more, or a plurality of the cells 46 defined by the struts or filaments 36. The covering or coating 40 may help reduce food impaction and/or tumor or tissue ingrowth. In some cases, the stent 10 may be a self-expanding stent (SES), although this is not required.

In some instances, in the radially expanded configuration, the stent 10 may include a first end region 20 proximate the proximal end 14 and a second end region 22 proximate the second end 16. In some embodiments, the first end region 20 and the second end region 22 may include retention features or anti-migration flared regions 24, 26 having enlarged diameters relative to the intermediate portion 18. The anti-migration flared regions 24, 26, which may be positioned adjacent to the first end 14 and the second end 16 of the stent 10, may be configured to engage an interior portion of the walls of the esophagus or other body lumen. In some embodiments, the retention features, or flared regions 24, 26 may have a larger diameter than the cylindrical intermediate region 18 of the stent 10 to prevent the stent 10 from migrating once placed in the esophagus or other body lumen. It is contemplated that the transition 28, 30 from the cross-sectional area of the intermediate region 18 to the retention features or flared regions 24, 26 may be gradual, sloped, or occur in an abrupt step-wise manner, as desired.

In some embodiments, the first anti-migration flared region 24 may have a first outer diameter and the second anti-migration flared region 26 may have a second outer diameter. In some instances, the first and second outer diameters may be approximately the same, while in other instances, the first and second outer diameters may be different. In some embodiments, the stent 10 may include only one or none of the anti-migration flared regions 24, 26. For example, the first end region 20 may include an anti-migration flare 24 while the second end region 22 may have an outer diameter similar to the intermediate region 18. It is further contemplated that the second end region 22 may include an anti-migration flare 26 while the first end region 20 may have an outer diameter similar to an outer diameter of the intermediate region 18. In some embodiments, the stent 10 may have a uniform outer diameter from the first end 14 to the second end 16. In some embodiments, the outer diameter of the intermediate region 18 may be in the range of about 15 to 25 millimeters. The outer diameter of the anti-migration flares 24, 26 may be in the range of about 20 to 30 millimeters. It is contemplated that the outer diameter of the stent 10 may be varied to suit the desired application. It is further contemplated that the stent 10 may include any number of changing features along its length such as, but not limited to, bumps, grooves, ridges, recesses, diameter changes, etc.

It is contemplated that the elongated tubular member of the stent 10 can be made from a number of different materials such as, but not limited to, metals, metal alloys, shape memory alloys and/or polymers, as desired, enabling the stent 10 to be expanded into shape when accurately positioned within the body. In some instances, the material may be selected to enable the stent 10 to be removed with relative ease as well. For example, the elongated tubular member of the stent 10 can be formed from alloys such as, but not limited to, nitinol and Elgiloy®. Depending on the material selected for construction, the stent 10 may be self-expanding or require an external force to expand the stent 10. In some embodiments, composite filaments may be used to make the stent 10, which may include, for example, an outer shell or cladding made of nitinol and a core formed of platinum or other radiopaque material. It is further contemplated the elongated tubular member of the stent 10 may be formed from polymers including, but not limited to, polyethylene terephthalate (PET). In some instances, the filaments of the stent 10, or portions thereof, may be bioabsorbable or biodegradable, while in other instances the filaments of the stent 10, or portions thereof, may be biostable.

Figure 2:
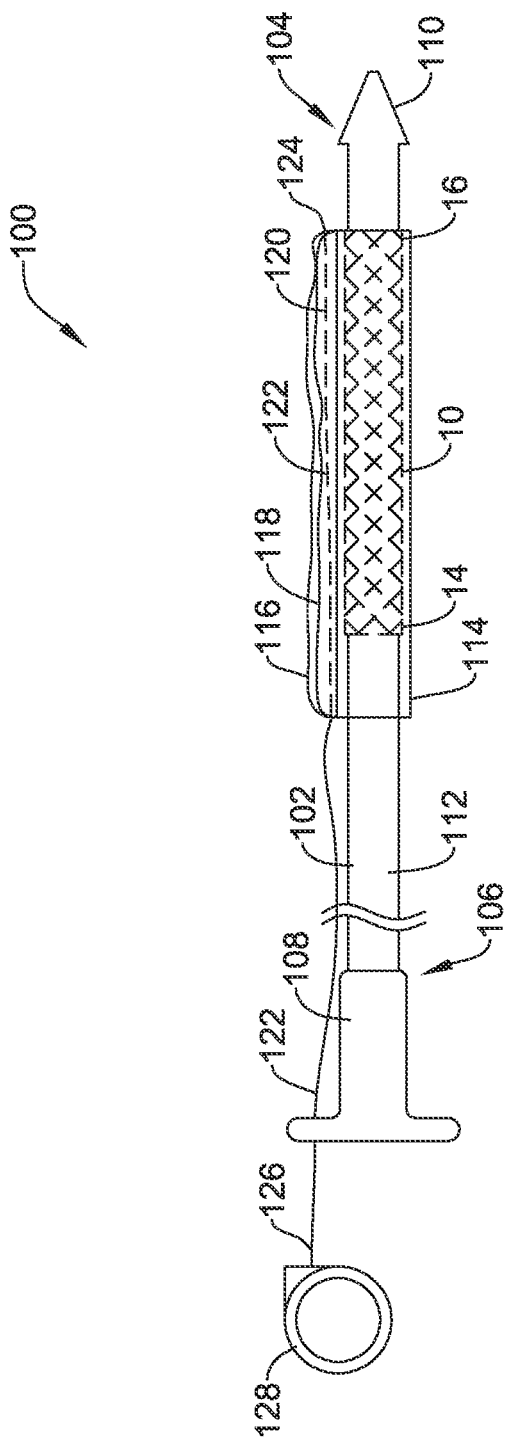
FIG. 2 is a side view of an illustrative delivery system for delivering the stent of FIG. 1.

FIG. 2 is a side view of an illustrative delivery system 100 for delivering a stent, such as the stent 10 described herein, to a target region. The delivery system 100 may include an elongate shaft or tubular member 102. The tubular member 102 may extend proximally from a distal end region 104 to a proximal end region 106 configured to remain outside of a patient's body. A hub or handle 108 may be coupled to the proximal end region 106 of the tubular member 102. The tubular member 102 may further include a distal tip 110 positioned adjacent to the distal end region 104. The distal tip 110 may be configured to be atraumatic.

The tubular member 102 may include a lumen 112 extending from the distal end region 104 to the proximal end region 106. The lumen 112 of the tubular member 102 may also extend through the handle 108. The lumen 112 of the tubular member 102 may be configured to receive a thread, pull-wire and/or guidewire, as desired.

The stent 10 may be disposed around a portion of the tubular member 102 at or adjacent to the distal end region 104 thereof. When the stent 10 is disposed over the tubular member 102, in a delivery configuration, the stent 10 may be restrained in a radially collapsed reduced diameter or delivery configuration by a sheath 114. The sheath 114 may be formed from a length of material, such as, but not limited to, an e-spun fabric (e.g. a polymer that has been formed into a fabric-like sheath), that has been wrapped around the stent 10 prior to deployment. The sheath 114 may be wrapped about the stent 10 such that the sheath 114 surrounds and covers the length of the stent 10 during delivery. The sheath 114 may have sufficient hoop strength to retain the stent 10 in its reduced diameter state.

The sheath 114 may be sutured or secured about the stent 10 with a thread 122 (e.g., filament or wire) along a seam 120 in a direction generally parallel to a longitudinal axis of the stent 10. The sheath 114 may be configured to apply a biasing force to the stent 10 which maintains the stent 10 in a collapsed or reduced diameter configuration. The thread 122 may be any thin flexible element capable of being sutured or sewn into the sheath 114. In some cases, a first lateral side 116 of the sheath 114 and a second lateral side 118 of the sheath 114 may extend from the seam 120. For example, the sheath 114 may be formed from a sheet of material or fabric with the longitudinally extending free ends 116, 118 sewn together along at the seam 120. The length of material between the seam 120 and the first and/or second lateral sides 116, 118 may be variable. The thread 122 may be sewn into the sheath 114 using a straight stitch which alternates between lateral sides of the sheath 114 and extends generally parallel to the longitudinal axis of the stent 10. In other cases, other stitches may be used, as desired, such as, but not limited to, a zigzag stitch, a double action stitch, a blanket stitch, etc. It is further contemplated that the seam 120 need not extend generally parallel to the longitudinal axis of the stent 10. For example, the seam 120 may be extend in a helical manner. It is further contemplated that more than one seam 120 may be used to secure the sheath 114. If so provided, two or more seams 120 may be uniformly spaced about the circumference of the sheath 114 or eccentrically spaced, as desired. In some cases, the seam 120 may extend less than an entire length of the sheath 114 or may extend along an entire length of the sheath 114, as desired.

The thread 122 may be sutured into the sheath 114 in a distal to proximal direction. For example, a knot 124 may be formed in the thread 122 and positioned adjacent to the distal end 16 of the stent 10. The seam 120 may then be stitched or sewn in a proximal direction. The reverse configuration is also contemplated in which the knot 124 is formed adjacent to the proximal end 14 of the stent 10 and the seam 120 sewn in a distal direction. It is contemplated that the positioning of the knot 124 may determine which portion of the stent 10 (e.g., proximal or distal) is expanded first. For example, as will be described in more detail herein, the distal end of the thread (e.g., adjacent to the knot 124) may be removed first thus deploying the portion of the stent 10 adjacent to the knot 124 first. The knot 124 may be similar in form and function to those used in knitting or crocheting, which allow the thread 122 to be releasably secured about the sheath 114. The knot 124 may generally maintain the thread 122 in a desired configuration while still allowing the thread 122 to be unraveled or removed as desired. In some cases, the thread 122 may not include the knot 124 or may include a plurality of knots 124, as desired.

In some cases, a tube or other more rigid component (not explicitly shown) may be positioned over the sheath 114 to help compress the stent 10 during suturing. Once the seam 120 is formed, the tube may be removed. The thread 122 may extend proximally along the exterior of the tubular member 102 to a proximal end 126 configured to remain outside the tubular member 102 and the body. The proximal end 126 of the thread 122 may be coupled to a pull member 128 or other actuation mechanism. The pull member 128, such as a pull ring, a pull tab, twist reel, or the like, may facilitate actuation of thread 122; however a pull member 128 or other actuation mechanism may not be present or required.

While the thread 122 is illustrated as extending proximally outside of the tubular member 102, in some cases, the tubular member 102 may include an opening, skive, slot, or port adjacent to the proximal end 14 of the stent 10 to allow the thread 122 to pass into the lumen 112. It is further contemplated that the tubular member 102 may include an opening, skive, slot, or port adjacent to the distal end 16 of the stent 10 to allow the thread 122 to pass into the lumen 112 when the thread 122 is sewn in a proximal to distal direction. If so provided, the opening may extend from an outer surface to an inner surface of the tubular member 102 to allow the thread 122 (or other components, as desired) to extend between the exterior of the tubular member 102 and the interior thereof.

Figure 3:
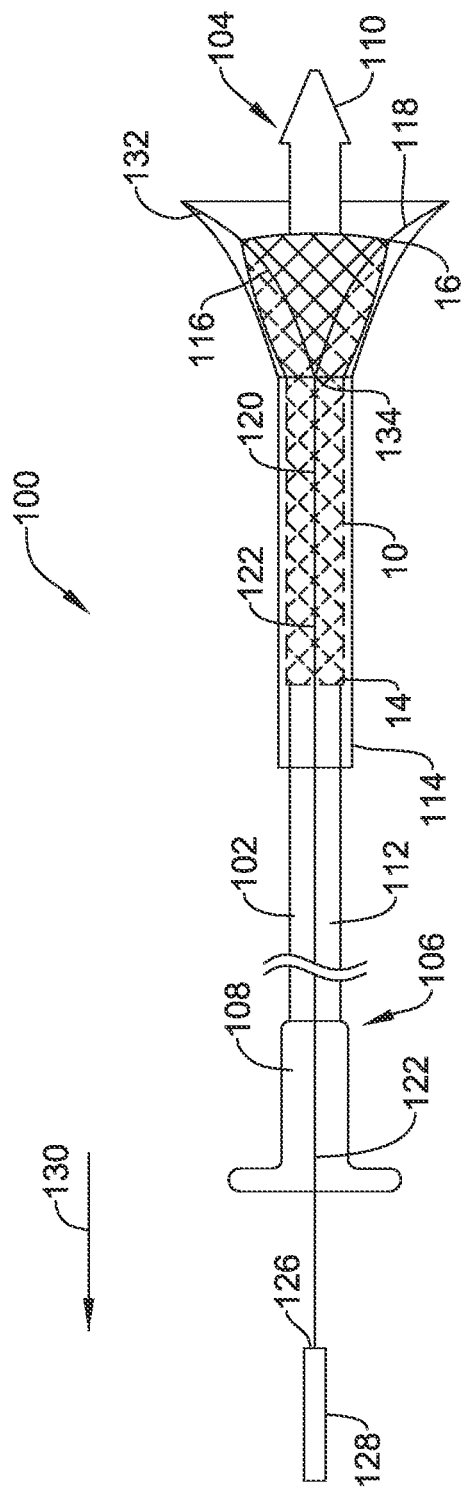
FIGS. 3-4 illustrate a method for delivering the illustrative implant of FIG. 1.
Figure 4:
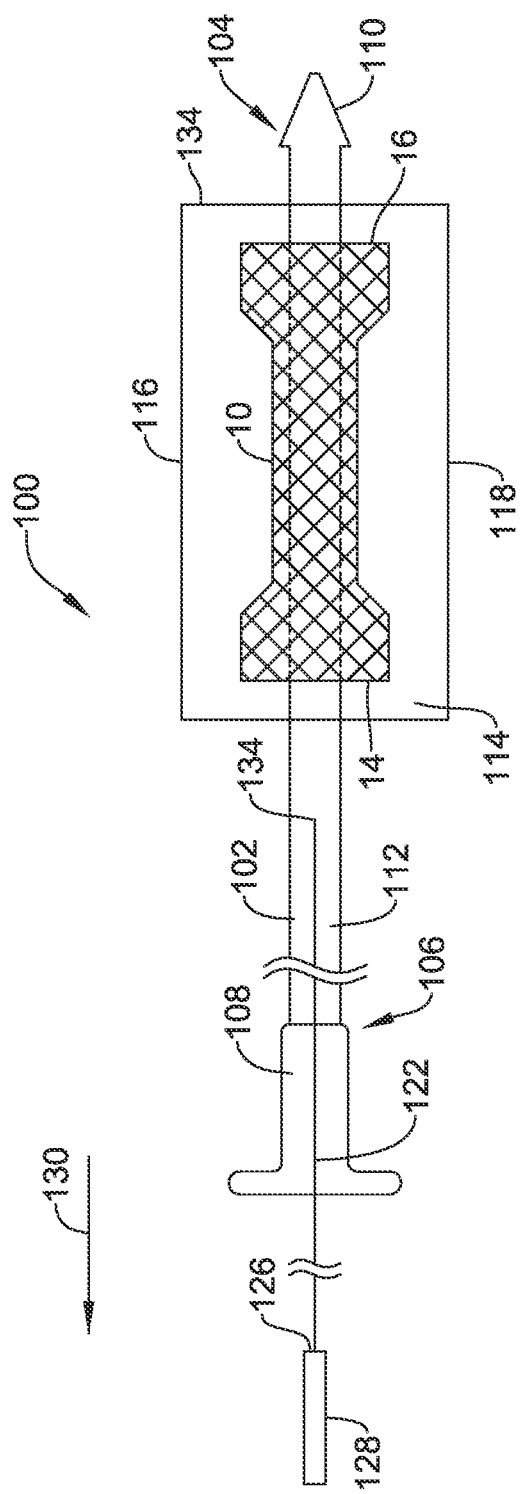

FIGS. 3-4 illustrate a top view of a method of delivering the illustrative stent 10 to a body lumen using the delivery device 100 of FIG. 2. The delivery device 100 may be advanced through the desired body lumen in any suitable manner. The delivery device 100 may be advanced with or without the use of a guidewire. Once the stent 10 is positioned adjacent to the target region, the restraining forces maintaining the stent 10 in the radially collapsed configuration may be removed.

Once the stent 10 is adjacent to the desired location, the knot 124 securing the thread 122 may be cut. However, in some cases, it may not be necessary to mechanically cut or remove the knot 124. For example, the knot 124 may be formed such that an applied force on the thread 122 is sufficient to unravel the knot. A proximal or pulling force 130 may then be applied to the proximal end 126 of the thread 122, as shown in FIG. 3. In some cases, the pulling force 130 may be applied by placing a finger inside of the pull member 128 and pulling away from the handle 108. As the member 128 is pulled or actuated, the thread 122 begins to snake through the sheath 114. In the embodiments shown in FIGS. 3-4, the thread 122 is sutured such that the thread 122 disposed over the distal end 16 of the stent 10 is removed or unraveled first. Still referring to FIG. 3, as the biasing force of the sheath 114 is released as the thread 122 is unraveled or proximally retracted 130, the distal end region 132 of the sheath 114 opens and the stent 10 begins to radially expand into its unbiased or deployed configuration. As the thread 122 is pulled, the distal end 134 of the thread 122 moves proximally through the seam 120. Continued proximal actuation of the thread 122 will cause more of the length of the stent 10 to be released. Proximal actuation of the proximal end 126 of the thread 122 may continue until the distal end 134 of the thread 122 has been completely removed from the sheath 114, or the seam 120 is completely removed, as shown in FIG. 4. It is contemplated that the clinician may continue to pull the thread 122 until the distal end 134 has been completely removed from the body and/or the device 100 although this is not required. As can be seen in FIG. 4, the sheath 114 is illustrated as having fallen away into a generally planar sheet. However, when in the body, the sheath 114 may retain a generally tubular configuration and may be positioned between the outer surface of the stent 10 and the body lumen. In some cases, the sheath 114 may be left in the body with the stent 10. In other embodiments, the sheath 114 may be removed using a removal tool, such as, but not limited to pinchers or clamps. In yet other embodiments, the thread 122 may remain attached to a portion of the sheath 114 such that the sheath 114 is proximally retracted with the thread 122.

Figure 5:
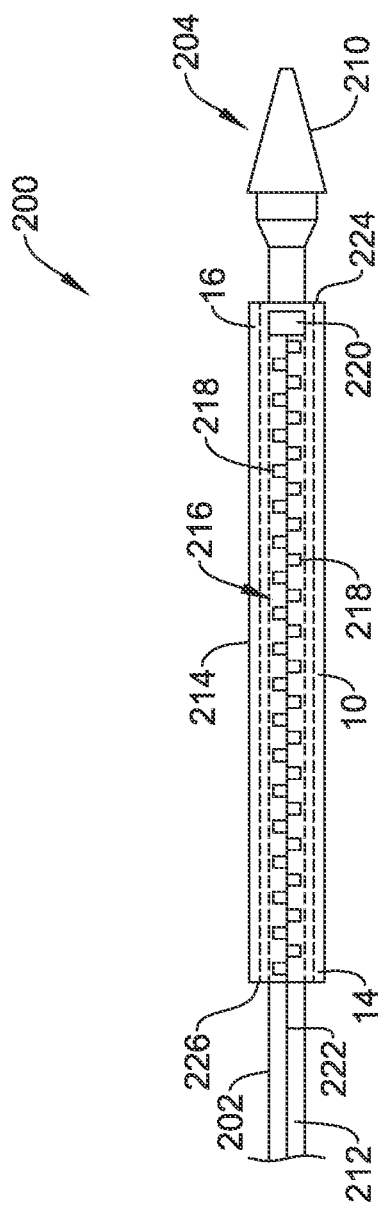
FIG. 5 is a partial side view of another illustrative delivery system for delivering the stent of FIG. 1.

FIG. 5 is a partial side view of another illustrative delivery system 200 for delivering a stent, such as the stent 10 described herein, to a target region. The delivery system 200 may include an elongate shaft or tubular member 202. The tubular member 202 may extend proximally from a distal end region 204 to a proximal end region (not explicitly shown) configured to remain outside of a patient's body. A hub or handle (not explicitly shown) may be coupled to the proximal end region of the tubular member 202. The tubular member 202 may further include a distal tip 210 positioned adjacent to the distal end region 204. The distal tip 210 may be configured to be atraumatic.

The tubular member 202 may include a lumen 212 extending from the distal end region 204 to the proximal end region. The lumen 212 of the tubular member 202 may also extend through the handle (if so provided). The lumen 212 of the tubular member 202 may be configured to receive a thread, pull-wire and/or guidewire, as desired.

The stent 10 may be disposed around a portion of the tubular member 202 at or adjacent to the distal end region 204 thereof. When the stent 10 is disposed over the tubular member 202, in a delivery configuration, the stent 10 may be restrained in a radially collapsed reduced diameter or delivery configuration by a sheath 214. The sheath 214 may be formed from a length of material, such as, but not limited to, a polymer or an e-spun fabric, that has been wrapped around the stent 10 prior to deployment. The sheath 214 may be wrapped about the stent 10 such that the sheath 214 surrounds and covers the length of the stent 10 during delivery. The sheath 214 may have sufficient hoop strength to retain the stent 10 in its reduced diameter state. The sheath 214 may be configured to apply a biasing force to the stent 10 which maintains the stent 10 in a collapsed or reduced diameter configuration.

The sheath 214 may be secured about the stent 10 with a zipper 216. The zipper 216 may include a plurality of teeth 218 that can be reversibly closed together with a slider 220. The slider 220 may be configured to be actuated in a direction generally parallel to a longitudinal axis of the stent 10 to close and open the zipper 216. The zipper 216 may be configured such that a proximal force is applied to the slider 220 to unzip the zipper 216. For example, the slider 220 may be coupled to a pull wire or string 222. The pull wire 222 may be any element capable of exerting a pulling or proximal force on the slider 220. In some cases, the pull wire 222 may be formed from a stiffer material or a tubular member configured to slide over the sheath 214 which allows for the user to apply a pushing or distal force on the slider 220. This may allow the stent 10 to be reconstrained, if so desired. It is further contemplated that the zipper 216 may be configured such that a distal pushing force will unzip the zipper 216. While not explicitly shown, the zipper 216 may include stops, insertion pins, retainer boxes, etc. to limit axial movement of the slider 220 and/or to facilitate zipping of the zipper 216. It is further contemplated that more than one zipper 216 may be used to secure the sheath 214. If so provided, two or more zippers 216 may be uniformly spaced about the circumference of the sheath 214 or eccentrically spaced, as desired. In some cases, the zipper 216 may extend less than an entire length of the sheath 214 or may extend along an entire length of the sheath 214, as desired.

It is contemplated that the direction in which the zipper 216 unzips may determine which portion of the stent 10 (e.g., proximal or distal) is expanded first. For example, as will be described in more detail herein, in the collapsed configuration, the slider 220 of the zipper 216 moves from the distal end 224 of the sheath 214 to the proximal end 226 of the sheath 214 thus deploying the distal end 16 of the stent 10 first. In some cases, a tube or other more rigid component (not explicitly shown) may be positioned over the sheath 214 to help compress the stent 10 during suturing. Once the zipper 216 is zipped or secured, the tube may be removed. The pull wire 222 may extend proximally along the exterior of the tubular member 202 to a proximal end (not explicitly shown) configured to remain outside the tubular member 202 and the body. The proximal end of the pull wire 222 may be coupled to a pull member (not explicitly shown) or other actuation mechanism. The pull member, such as a pull ring, a pull tab, twist reel, or the like, may facilitate actuation of pull wire 222; however a pull member or other actuation mechanism may not be present or required.

While the pull wire 222 is illustrated as extending proximally outside of the tubular member 202, in some cases, the tubular member 202 may include an opening, skive, slot, or port adjacent the proximal end 14 of the stent 10 to allow the pull wire 222 to pass into the lumen 212. If so provided, the opening may extend from an outer surface to an inner surface of the tubular member 202 to allow the pull wire 222 (or other components, as desired) to extend between the exterior of the tubular member 202 and the interior thereof.

Figure 6:
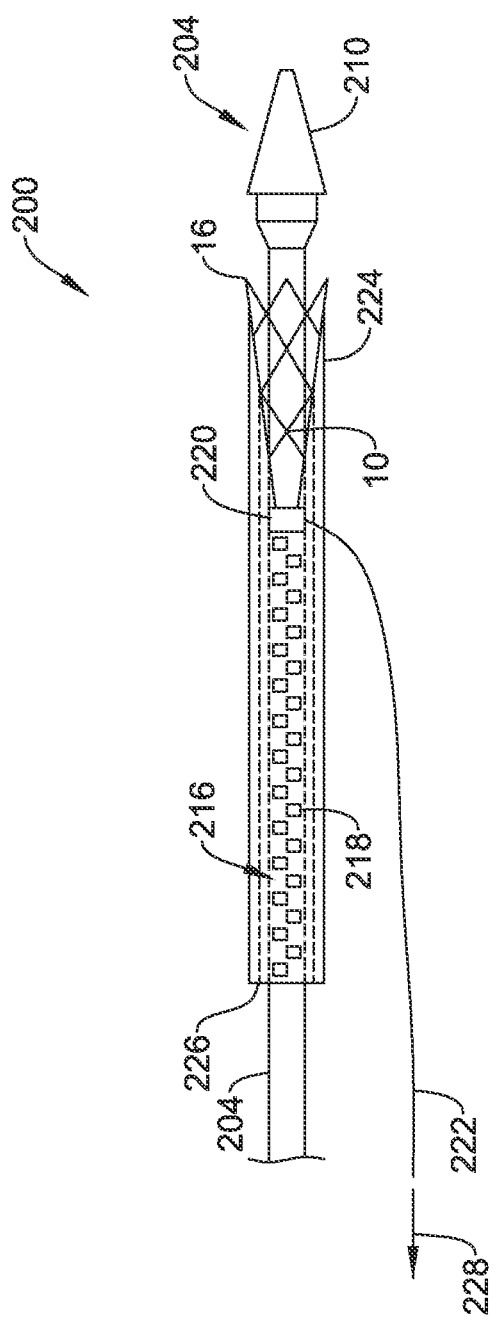
FIGS. 6-7 illustrate another example method for delivering the illustrative implant of FIG. 1.
Figure 7:
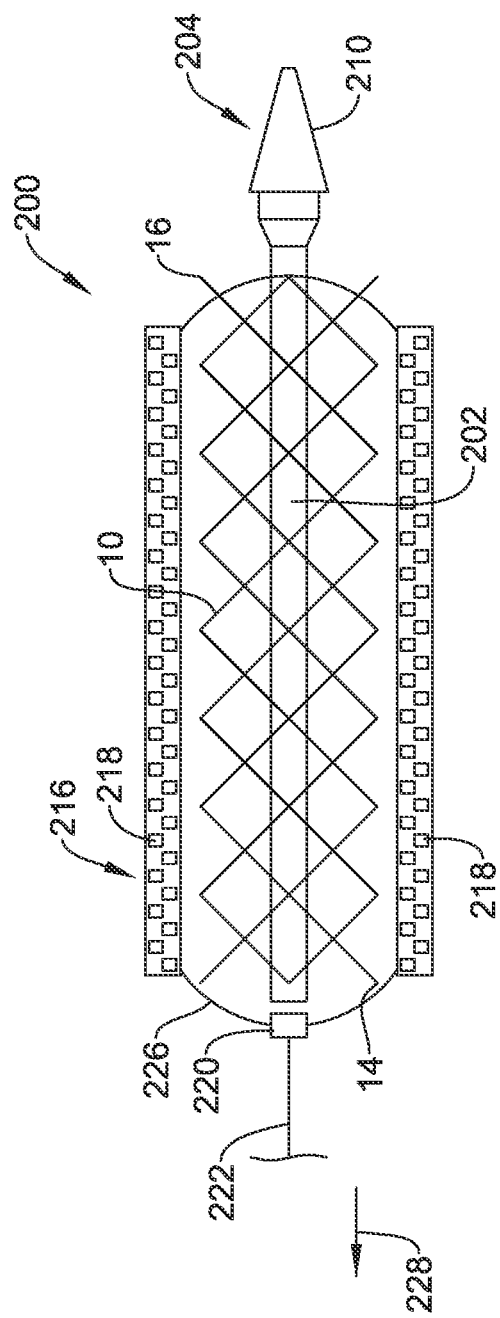

FIGS. 6-7 illustrate a method of delivering the illustrative stent 10 to a body lumen using the delivery device 200 of FIG. 5. The delivery device 200 may be advanced through the desired body lumen in any suitable manner. The delivery device 200 may be advanced with or without the use of a guidewire. Once the stent 10 is positioned adjacent to the target region, the restraining forces maintaining the stent 10 in the radially collapsed configuration may be removed.

Once the stent 10 is adjacent to the desired location, a proximal or pulling force 228 may then be applied to the proximal end of the pull wire 222, as shown in FIG. 6. In some cases, the pulling force 228 may be applied by placing a finger inside of the pull member and pulling away from the handle. As the proximal end of the pull wire 222 is pulled or actuated, the slider 220 begins to move proximally and starts to unzip the zipper 216, as shown in FIG. 6. In the embodiments shown in FIGS. 6-7, the zipper 216 is configured such that the slider 220 is adjacent to the distal end 16 of the stent 10 and proximal actuation thereof exposes the distal end 16 of the stent 10 first. Still referring to FIG. 6, as the biasing force of the sheath 214 is released as the slider 220 is proximally retracted 228, the distal end region 224 of the sheath 214 opens and the stent 10 begins to radially expand into its unbiased or deployed configuration. As the pull wire 222 is pulled, the slider 220 moves proximally along the teeth 218 of the zipper 216. Continued proximal actuation of the pull wire 222 will cause more of the length of the stent 10 to be released. Proximal actuation of the proximal end of the pull wire 222 may continue until the slider 220 engages a retainer box or other stop mechanism, as shown in FIG. 7. It is contemplated that the clinician may continue to pull the pull wire 222 until the slider 220 has been completely removed from the body and/or the device 200 although this is not required. It is contemplated that if the slider 220 is interlocked with the sheath 214 via the zipper 216, the sheath 214 may be removed with the slider 220 through continued proximal actuation of the pull wire 222. When in the body, the sheath 214 may retain a generally tubular configuration and may be positioned between the outer surface of the stent 10 and the body lumen. In some cases, the sheath 214 may be left in the body with the stent 10. In other embodiments, as described herein, the pull wire 222 may remain attached to a portion of the sheath 214 such that the sheath 214 is proximally retracted with the pull wire 222. In yet other embodiments, the sheath 214 may be removed using a removal tool, such as, but not limited to pinchers or clamps.

Figure 8:
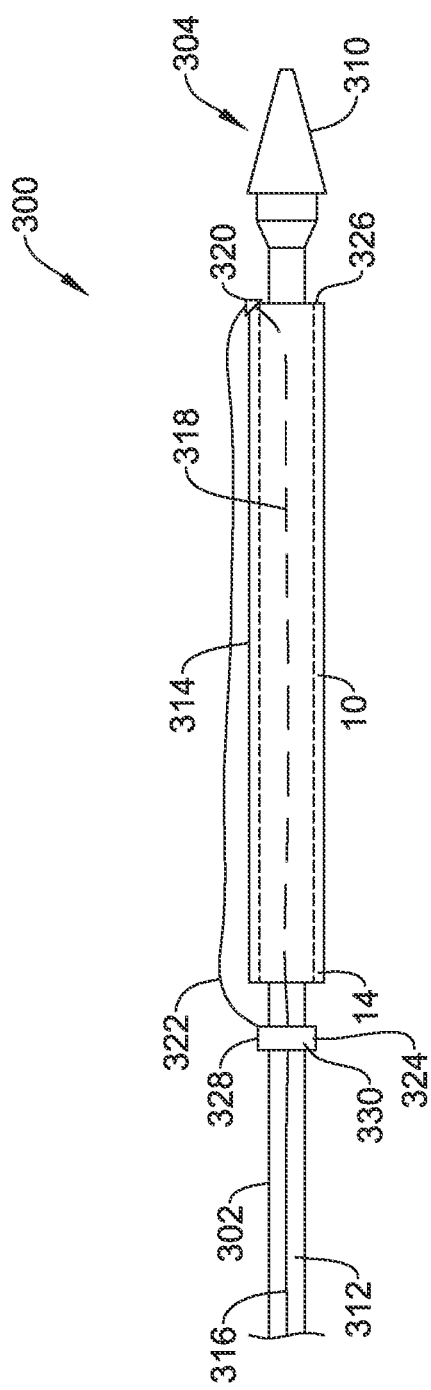
FIG. 8 is a partial side view of another illustrative delivery system for delivering the stent of FIG. 1.

FIG. 8 is a partial side view of another illustrative delivery system 300 for delivering a stent, such as the stent 10 described herein, to a target region. The delivery system 300 may include an elongate shaft or tubular member 302. The tubular member 302 may extend proximally from a distal end region 304 to a proximal end region (not explicitly shown) configured to remain outside of a patient's body. A hub or handle (not explicitly shown) may be coupled to the proximal end region of the tubular member 302. The tubular member 302 may further include a distal tip 310 positioned adjacent to the distal end region 304. The distal tip 310 may be configured to be atraumatic.

The tubular member 302 may include a lumen 312 extending from the distal end region 304 to the proximal end region. The lumen 312 of the tubular member 302 may also extend through the handle (if so provided). The lumen 312 of the tubular member 302 may be configured to receive a thread, pull-wire and/or guidewire, as desired.

The stent 10 may be disposed around a portion of the tubular member 302 at or adjacent to the distal end region 304 thereof. When the stent 10 is disposed over the tubular member 302, in a delivery configuration, the stent 10 may be restrained in a radially collapsed reduced diameter or delivery configuration by a sheath 314. The sheath 314 may be formed from a length of material, such as, but not limited to, a polymer or an e-spun fabric, that has been wrapped around the stent 10 prior to deployment. The material for the sheath 314 may be selected such that the sheath 314 can retain the stent 10 but readily release the stent 10 when torn. The sheath 314 may be wrapped about the stent 10 such that the sheath 314 surrounds and covers the length of the stent 10 during delivery. The sheath 314 may have sufficient hoop strength to retain the stent 10 in its reduced diameter state. The sheath 314 may be configured to apply a biasing force to the stent 10 which maintains the stent 10 in a collapsed or reduced diameter configuration. In some cases, the sheath 314 may be formed from a sheet of material and sutured in a similar manner to the sheath 114 described with respect to FIG. 2. In other embodiments, the sheath 314 may be heat shrunk or otherwise formed over the stent 10.

The delivery system 300 may further include a cutting wire 316 configured to tear or cut the sheath 314. The cutting wire 316 may be any element capable of exerting a tearing force on the sheath 314. The sheath 314 may be wrapped about an intermediate region 318 of the cutting wire 316 such that at least a portion of the cutting wire 316 is disposed radially between the stent 10 and the sheath 314. The distal end region 322 of the cutting wire 316 may exit from the distal end 326 of the sheath 314 and extend proximally along an outer surface of the sheath 314. The orientation of the cutting wire 316 may be reversed such that the distal end region 322 is radially disposed between the sheath 314 and the stent 10 and the intermediate region 318 is radially exterior to the sheath 314. The distal end 328 of the cutting wire 316 may be fixedly secured to a stopper or cap 324. The intermediate region 318 of the cutting wire 316 may be slidably disposed within or through a lumen 330 of the cap 324. It is further contemplated that more than one cutting wire 316 may be used to cut or tear the sheath 314. If so provided, two or more cutting wires 316 may be uniformly spaced about the circumference of the sheath 314 or eccentrically spaced, as desired. Further, if more than one cutting wire 316 is provided, the cutting wires 316 may be actuated together or one after the other.

The cutting wire 316 may further include a cutting element 320 fixedly coupled to intermediate region 318 of the cutting wire 316. In some embodiments, the cutting element 320 may be positioned radially outward of the sheath 314 with the cutting surface extending radially inward. In other embodiments, the cutting element 320 may be positioned radially inward of the sheath 314 with the cutting surface extending radially outwards. The cutting element 320 may be a blade, a pair of blades hinged like scissors, a toothed blade, etc. The cutting element 320 may be configured to cut or tear the sheath 314 as the intermediate region 318 is proximally retracted.

The cutting wire 316 may extend proximally along the exterior of the tubular member 302 to a proximal end (not explicitly shown) configured to remain outside the tubular member 302 and the body. The proximal end of the cutting wire 316 may be coupled to a pull member (not explicitly shown) or other actuation mechanism. The pull member, such as a pull ring, a pull tab, twist reel, or the like, may facilitate actuation of cutting wire 316; however a pull member or other actuation mechanism may not be present or required.

While the cutting wire 316 is illustrated as extending proximally outside of the tubular member 302, in some cases, the tubular member 302 may include an opening, skive, slot, or port adjacent the proximal end 14 of the stent 10 to allow the cutting wire 316 to pass into the lumen 312. If so provided, the opening may extend from an outer surface to an inner surface of the tubular member 302 to allow the cutting wire 316 (or other components, as desired) to extend between the exterior of the tubular member 302 and the interior thereof.

Figure 9:
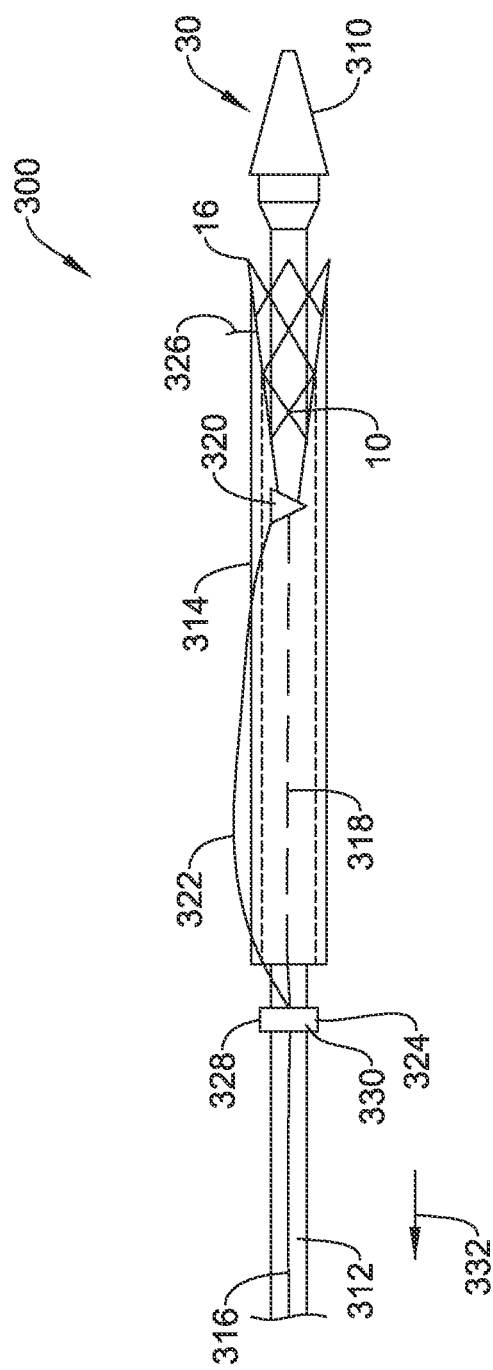
FIG. 9 illustrates another example method for delivering the illustrative implant of FIG. 1.

FIG. 9 illustrates a method of delivering the illustrative stent 10 to a body lumen using the delivery device 300 of FIG. 8. The delivery device 300 may be advanced through the desired body lumen in any suitable manner. The delivery device 300 may be advanced with or without the use of a guidewire. Once the stent 10 is positioned adjacent to the target region, the restraining forces maintaining the stent 10 in the radially collapsed configuration may be removed.

Once the stent 10 is adjacent to the desired location, a proximal or pulling force 332 may then be applied to the proximal end of the cutting wire 316, as shown in FIG. 9. In some cases, the pulling force 332 may be applied by placing a finger inside of a pull member and pulling away from the handle. As the proximal end of the cutting wire 316 is pulled or actuated, the intermediate region 318 and the cutting element 320 begin to move proximally and the cutting element 320 starts to cut the sheath 314, as shown in FIG. 9. In the embodiments shown in FIG. 9, the cutting element 320 is configured such that the cutting element 320 is adjacent to the distal end 16 of the stent 10 and proximal actuation thereof exposes the distal end 16 of the stent 10 first. As the biasing force of the sheath 314 is released as the cutting element 320 is proximally retracted 332, the distal end region 326 of the sheath 314 opens and the stent 10 begins to radially expand into its unbiased or deployed configuration. As the cutting wire 316 is pulled, the cutting element 320 tears, cuts, or slices the sheath 314. In some embodiments, the sheath 314 may be perforated to facilitate tearing of the sheath 314. It is contemplated that the size of the cutting element 320 may be selected such that the cutting element 320 is free from contact with the outer surface of the stent 10.

Continued proximal actuation of the cutting wire 316 will cause more of the length of the stent 10 to be released. Proximal actuation of the proximal end of the cutting wire 316 may continue until the cutting element 320 engages the cap 324. The cap 324 may be configured to remain longitudinally fixed until the cutting element 320 is engaged therewith. For example, the cap 324 may be configured seal the cutting surface of the cutting element 320 such that the cutting element 320 can be safely removed from the body. It is contemplated that the clinician may continue to pull the cutting wire 316 until the cutting element 320 has been completely removed from the body and/or the device 300 although this is not required. It is contemplated that if the cap 324 and/or cutting element 320 is mechanically coupled with the sheath 314, the sheath 314 may be removed with the cutting element 320 and/or cap 324 through continued proximal actuation of the cutting wire 316. When in the body, the sheath 314 may retain a generally tubular configuration and may be positioned between the outer surface of the stent 10 and the body lumen. In some cases, the sheath 314 may be left in the body with the stent 10. In other embodiments, as described herein, the cutting wire 316 may remain attached to a portion of the sheath 314 such that the sheath 314 is proximally retracted with the cutting wire 316. In yet other embodiments, the sheath 314 may be removed using a removal tool, such as, but not limited to pinchers or clamps.

Figure 10:
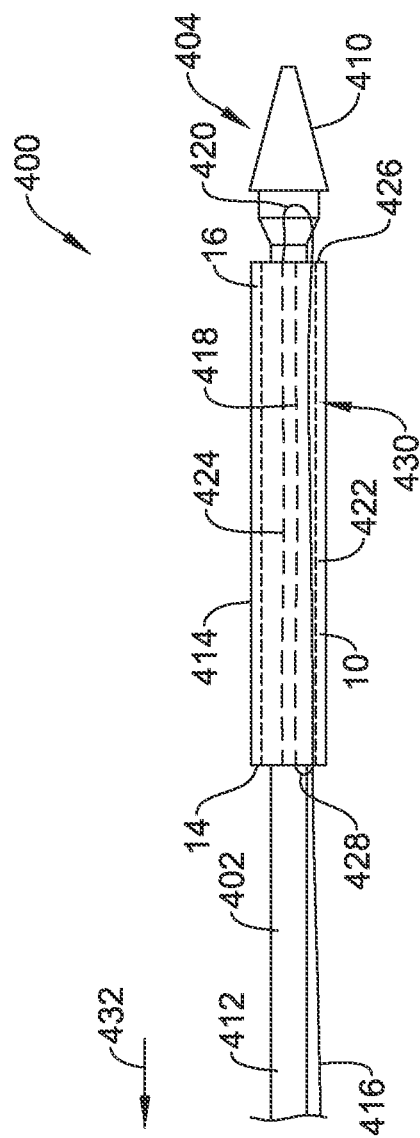
FIG. 10 is a partial side view of another illustrative delivery system for delivering the stent of FIG. 1.

FIG. 10 is a partial side view of another illustrative delivery system 400 for delivering a stent, such as the stent 10 described herein, to a target region. The delivery system 400 may include an elongate shaft or tubular member 402. The tubular member 402 may extend proximally from a distal end region 404 to a proximal end region (not explicitly shown) configured to remain outside of a patient's body. A hub or handle (not explicitly shown) may be coupled to the proximal end region of the tubular member 402. The tubular member 402 may further include a distal tip 410 positioned adjacent to the distal end region 404. The distal tip 410 may be configured to be atraumatic.

The tubular member 402 may include a lumen 412 extending from the distal end region 404 to the proximal end region. The lumen 412 of the tubular member 402 may also extend through the handle (if so provided). The lumen 412 of the tubular member 402 may be configured to receive a thread, pull-wire and/or guidewire, as desired.

The stent 10 may be disposed around a portion of the tubular member 402 at or adjacent to the distal end region 404 thereof. When the stent 10 is disposed over the tubular member 402, in a delivery configuration, the stent 10 may be restrained in a radially collapsed reduced diameter or delivery configuration by a sheath 414. The sheath 414 may be formed from a length of material, such as, but not limited to, a polymer or an e-spun fabric, that has been wrapped around the stent 10 prior to deployment. The material for the sheath 414 may be selected such that the sheath 414 can retain the stent 10 but readily release the stent 10 when torn. The sheath 414 may be wrapped about the stent 10 such that the sheath 414 surrounds and covers the length of the stent 10 during delivery. The sheath 414 may have sufficient hoop strength to retain the stent 10 in its reduced diameter state. The sheath 414 may be configured to apply a biasing force to the stent 10 which maintains the stent 10 in a collapsed or reduced diameter configuration. In some cases, the sheath 414 may be formed from a sheet of material and sutured in a similar manner to the sheath 114 described with respect to FIG. 2. In other embodiments, the sheath 414 may be heat shrunk or otherwise formed over the stent 10.

Figure 11:
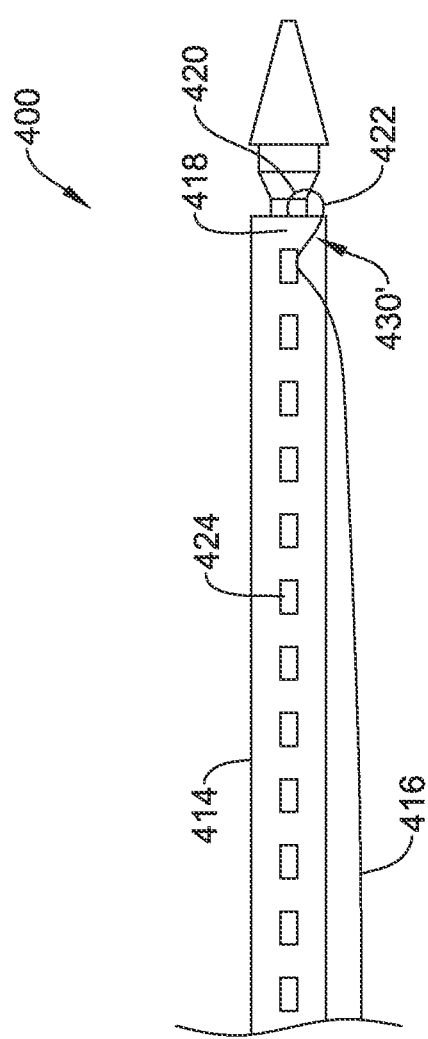
FIG. 11 is a partial side view of another illustrative delivery system for delivering the stent of FIG. 1.

The delivery system 400 may further include a cutting wire 416 configured to tear or cut the sheath 414. The cutting wire 416 may be any element capable of exerting a tearing force on the sheath 414. The sheath 414 may be wrapped about an intermediate region 418 of the cutting wire 416 such that at least a portion of the cutting wire 416 is disposed radially between the stent 10 and the sheath 414. The distal end region 422 of the cutting wire 416 may exit from the distal end 426 of the sheath 414 and extend proximally along an outer surface of the sheath 414. The orientation of the cutting wire 416 may be reversed such that the distal end region 422 is radially disposed between the sheath 414 and the stent 10 and the intermediate region 418 is radially exterior to the sheath 414. The distal end 428 of the cutting wire 416 may be fixedly secured to cutting wire 416 proximal to the intermediate region 418 to form a loop 430. The distal end 420 of the loop 430 may be configured to cut or tear the sheath 414 as the intermediate region 418 is proximally retracted. In some embodiment, the loop 430 may extend over an entire length of the sheath 414. In other embodiments, the loop 430 may have a length that is less than a length of the sheath 414. For example, FIG. 11 illustrates a loop 430' that is less than entire length of the sheath 414. It is contemplated that in some instances, a smaller loop 430' may provide a more controlled cutting area. While not explicitly shown, the distal ends 420 of the loops 430, 430' may be provided with a cutting element such that the cutting wire 416 may both cut and pull the sheath 414. It is further contemplated that more than one cutting wire 416 may be used to cut or tear the sheath 414. If so provided, two or more cutting wires 416 may be uniformly spaced about the circumference of the sheath 414 or eccentrically spaced, as desired. Further, if more than one cutting wire 416 is provided, the cutting wires 416 may be actuated together or one after the other.

In some embodiments, the sheath 414 may include perforations 424 extending along a length thereof. The perforations 424 may extend generally parallel to a longitudinal axis of the stent 10, although this is not required. For example, the perforations 424 may extend in a helical configuration, if so desired. It is further contemplated that more than one set of perforations 424 may be provided. In some cases, the perforations 424 may extend less than an entire length of the sheath 414 or may extend along an entire length of the sheath 414, as desired.

The loop 430 of the cutting wire 416 may be generally circumferentially aligned with the perforations 424. The cutting wire 416 may extend proximally along the exterior of the tubular member 402 to a proximal end (not explicitly shown) configured to remain outside the tubular member 402 and the body. The proximal end of the cutting wire 416 may be coupled to a pull member (not explicitly shown) or other actuation mechanism. The pull member, such as a pull ring, a pull tab, twist reel, or the like, may facilitate actuation of cutting wire 416; however a pull member or other actuation mechanism may not be present or required.

While the cutting wire 416 is illustrated as extending proximally outside of the tubular member 402, in some cases, the tubular member 402 may include an opening, skive, slot, or port adjacent the proximal end 14 of the stent 10 to allow the cutting wire 416 to pass into the lumen 412. If so provided, the opening may extend from an outer surface to an inner surface of the tubular member 402 to allow the cutting wire 416 (or other components, as desired) to extend between the exterior of the tubular member 402 and the interior thereof.

The delivery device 400 may be advanced through the desired body lumen in any suitable manner. The delivery device 400 may be advanced with or without the use of a guidewire. Once the stent 10 is positioned adjacent to the target region, the restraining forces maintaining the stent 10 in the radially collapsed configuration may be removed.

Once the stent 10 is adjacent to the desired location, a proximal or pulling force 432 may then be applied to the proximal end of the cutting wire 416. In some cases, the pulling force 432 may be applied by placing a finger inside of a pull member and pulling away from the handle. As the proximal end of the cutting wire 416 is pulled or actuated, the intermediate region 418 and the distal end 420 of the loop 430 begin to move proximally and the distal end 420 of the loop 430 starts to cut the sheath 414. The loop 430 is configured such that the distal end 420 thereof is adjacent to the distal end 16 of the stent 10 and proximal actuation thereof exposes the distal end 16 of the stent 10 first. As the biasing force of the sheath 414 is released as the loop 430 is proximally retracted 432, the distal end region 426 of the sheath 414 opens and the stent 10 begins to radially expand into its unbiased or deployed configuration. As the cutting wire 416 is pulled, the distal end 420 of the loop 430 tears, cuts, or slices the sheath 414.

Continued proximal actuation of the cutting wire 416 will cause more of the length of the stent 10 to be released. Proximal actuation of the proximal end of the cutting wire 416 may continue until the distal end 420 of the loop 430 engages a proximal end 434 of the sheath 414. It is contemplated that the clinician may continue to pull the cutting wire 416 until the loop 430 has been completely removed from the body and/or the device 400 although this is not required. It is contemplated that if the loop is mechanically coupled with the sheath 414, the sheath 414 may be removed with the cutting wire 416 through continued proximal actuation of the cutting wire 416. When in the body, the sheath 414 may retain a generally tubular configuration and may be positioned between the outer surface of the stent 10 and the body lumen. In some cases, the sheath 414 may be left in the body with the stent 10. In other embodiments, as described herein, the cutting wire 416 may remain attached to a portion of the sheath 414 such that the sheath 414 is proximally retracted with the cutting wire 416. In yet other embodiments, the sheath 414 may be removed using a removal tool, such as, but not limited to pinchers or clamps.

Figure 12:
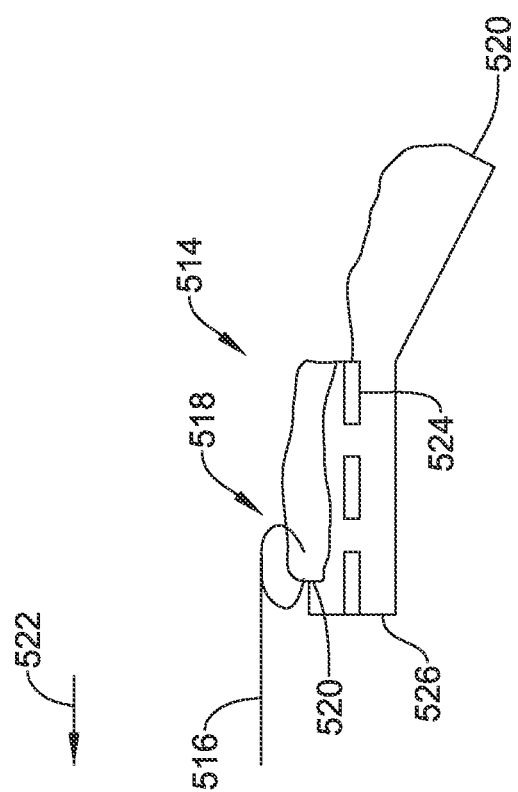
FIG. 12 is a partial side view of an illustrative sheath for releasing the stent of FIG. 1.

FIG. 12 illustrates a side view of another illustrative removable sheath 514 that may be used to retain a stent, such as the stent 10 described herein, on or within a delivery system. While not explicitly shown, the sheath 514 may be used with any of the delivery systems described herein. When the stent is in a delivery configuration, the stent may be restrained in a radially collapsed reduced diameter or delivery configuration by a sheath 514. The sheath 514 may be formed from a length of material, such as, but not limited to, a polymer or an e-spun fabric, that has been wrapped around the stent prior to deployment. The material for the sheath 514 may be selected such that the sheath 514 can retain the stent 10 but readily release the stent 10 when torn. The sheath 514 may be wrapped about the stent such that the sheath 514 surrounds and covers the length of the stent during delivery. The sheath 514 may have sufficient hoop strength to retain the stent in its reduced diameter state. The sheath 514 may be configured to apply a biasing force to the stent which maintains the stent in a collapsed or reduced diameter configuration. In some cases, the sheath 514 may be formed from a sheet of material and sutured in a similar manner to the sheath 114 described with respect to FIG. 2. In other embodiments, the sheath 514 may be heat shrunk or otherwise formed over the stent.

In some embodiments, the sheath 514 may include perforations 524 extending along a length thereof. The perforations 524 may extend generally parallel to a longitudinal axis of the sheath 514, although this is not required. In some embodiments, the perforations 524 may extend in a generally helical configuration. It is further contemplated that more than one set of perforations 524 may be provided. The perforations 524 may be configured to facilitate tearing of the sheath 514 along a length thereof. In some cases, the length and/or width of the perforations 524 may be varied. In some cases, the perforations 524 may extend less than an entire length of the sheath 514 or may extend along an entire length of the sheath 514, as desired.

It is contemplated that the sheath 514 may be torn with a clip 518 that is attached to a wire 516. For example, the clip 518 may include pinchers or other grasping mechanisms that are configured to grip or grasp a distal end 520 (or a proximal end 526, if so desired) of the sheath 514. The wire 516 may extend proximally form the clip 518 to a proximal end (not explicitly shown) configured to remain outside the body. The proximal end of the wire 516 may be coupled to a pull member (not explicitly shown) or other actuation mechanism. The pull member, such as a pull ring, a pull tab, twist reel, or the like, may facilitate actuation of wire 516; however a pull member or other actuation mechanism may not be present or required.

To deploy the stent at a desired, target location, the user may grip the distal end 520 of the sheath 514 within the clip 518. With the distal end 520 of the sheath 514 gripped within the clip 518, the wire 516 can be proximally retracted to tear the sheath 514. In some cases, a pulling force 522 may be applied by placing a finger inside of a pull member and pulling away from the handle. As the proximal end of the wire 516 is pulled or actuated, the clip 518 moves proximally as well and beings to tear cut the sheath 514, as shown in FIG. 12. In the embodiments shown in FIG. 12, the clip 518 is gripping the distal end 520 of the sheath 514 such proximal actuation of the wire 516 exposes the distal end 16 of the stent 10 first. As the biasing force of the sheath 514 is released as the wire 516 is proximally retracted 522, the distal end region 520 of the sheath 514 opens and the stent can begin to radially expand into its unbiased or deployed configuration.

Continued proximal actuation of the wire 516 will cause more of the length of the stent 10 to be released. Proximal actuation of the proximal end of the wire 516 may continue until the stent is fully deployed. It is contemplated that the clinician may continue to pull the wire 516 until the clip 518 and sheath 514 (or a portion thereof) has been completely removed from the body and/or the delivery device although this is not required. In some cases, the wire 516 and clip 518 can be used to retrieve any remnants of the sheath 514 that remains in the body. When in the body, the sheath 514 may retain a generally tubular configuration and may be positioned between the outer surface of the stent 10 and the body lumen. In some cases, the sheath 514, or portions thereof, may be left in the body with the stent.

Figure 13:
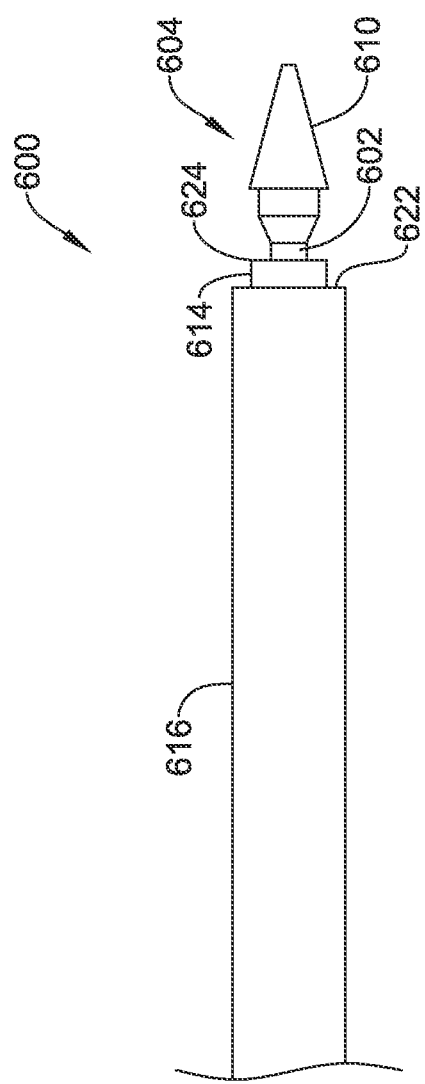
FIG. 13 is a partial side view of another illustrative delivery system for delivering the stent of FIG. 1.

FIG. 13 is a side view of another illustrative delivery system 600 for delivering a stent, such as the stent 10 (see, for example, FIG. 15) described herein, to a target region. The delivery system 600 may include an elongate shaft or inner tubular member 602. The inner tubular member 602 may extend proximally from a distal end region 604 to a proximal end region (not explicitly shown) configured to remain outside of a patient's body. A hub or handle (not explicitly shown) may be coupled to the proximal end region of the inner tubular member 602. The inner tubular member 602 may further include a distal tip 610 positioned adjacent to the distal end region 604. The distal tip 610 may be configured to be atraumatic.

The inner tubular member 602 may include a lumen (not explicitly shown) extending from the distal end region 604 to the proximal end region. The lumen of the inner tubular member 602 may also extend through the handle (if so provided). The lumen of the inner tubular member 602 may be configured to receive a thread, pull-wire and/or guidewire, as desired.

The stent 10 may be disposed around a portion of the inner tubular member 602 at or adjacent to the distal end region 604 thereof. When the stent 10 is disposed over the inner tubular member 602, in a delivery configuration, the stent 10 may be restrained in a radially collapsed reduced diameter or delivery configuration by a sheath 614. The sheath 614 may be formed from a length of material, such as, but not limited to, a polymer or an e-spun fabric, that has been wrapped around the stent 10 prior to deployment. The material for the sheath 614 may be selected such that the sheath 614 can retain the stent 10 but readily release the stent 10 when torn. The sheath 614 may be wrapped about the stent 10 such that the sheath 614 surrounds and covers the length of the stent 10 during delivery. The sheath 614 may have sufficient hoop strength to retain the stent 10 in its reduced diameter state. The sheath 614 may be configured to apply a biasing force to the stent 10 which maintains the stent 10 in a collapsed or reduced diameter configuration. In some cases, the sheath 614 may be formed from a sheet of material and sutured in a similar manner to the sheath 114 described with respect to FIG. 2. In other embodiments, the sheath 614 may be heat shrunk or otherwise formed over the stent 10.

Figure 14:
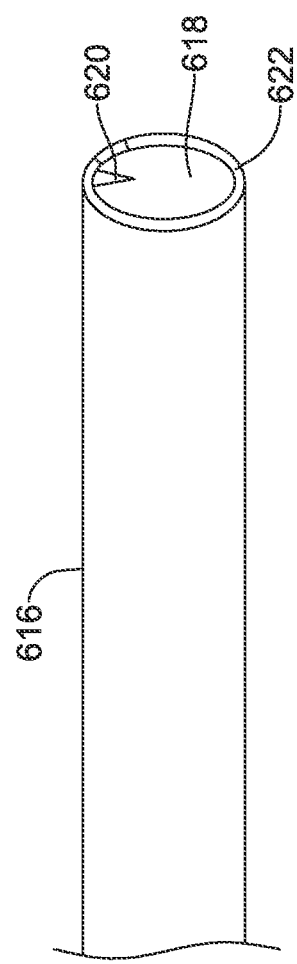
FIG. 14 is a partial perspective view of the sheath of FIG. 13.

The delivery system 600 may further include an outer tubular member 616 configured to tear or cut the sheath 614. Referring additionally to FIG. 14, which illustrates a partial perspective view of the illustrative outer tubular member 616, the outer tubular member 616 may define a lumen extending from a distal end 622 to a proximal end (not explicitly shown) configured to remain outside the body. The proximal end of the outer tubular member 616 may be coupled to a handle to facilitate actuation of the outer tubular member 616. The outer tubular member 616 may include a lumen 618 extending from the distal end 622 to the proximal end. The lumen 618 of the outer tubular member 616 may also extend through a handle (if so provided). The lumen 618 of the tubular member 616 may be configured to be slidably disposed over the sheath 614 and inner tubular member 602. In some cases, the outer tubular member 616 may be configured to extend over substantially an entire length of the inner tubular member 602. The outer tubular member 616 may further include a cutting element 620 fixedly secured to an inner surface of the outer tubular member 616. The cutting element 620 may be glued, adhered, molded into, hot melted, etc. into the outer tubular member 616, as desired. The cutting element 620 may extend radially inward into the lumen 618. It is contemplated that the cutting element 620 may be a blade, a small pick, a saw tooth blade, two blades secured together to form a "V" shaped cutting surface (e.g., in an open scissors manner), etc. The cutting element 620 may be configured to cut or tear the sheath 614 to deploy the stent 10. In some cases, the outer tubular member 616 may include more than one cutting element 620. If more than one cutting element 620 is provided, the cutting elements 620 need not be of the same type. It is further contemplated that the cutting elements 620 may be uniformly spaced about the inner surface of the outer tubular member 616 or eccentrically spaced, as desired.

The outer tubular member 616 may be sized and shaped to minimize friction between the inner surface of the outer tubular member 616 and the outer surface of the sheath 614 and/or inner tubular member 602. For example, the inner diameter of the outer tubular member 616 may be greater than the outer diameter of the sheath 614 when it is disposed over the stent 10. It is further contemplated that the radial height of the cutting element 620 may be selected such that the cutting element 620 is radially spaced from the stent 10 so as to leave the stent 10 untouched when the outer tubular member 616 is longitudinally actuated, as will be described in more detail herein.

Figure 15:
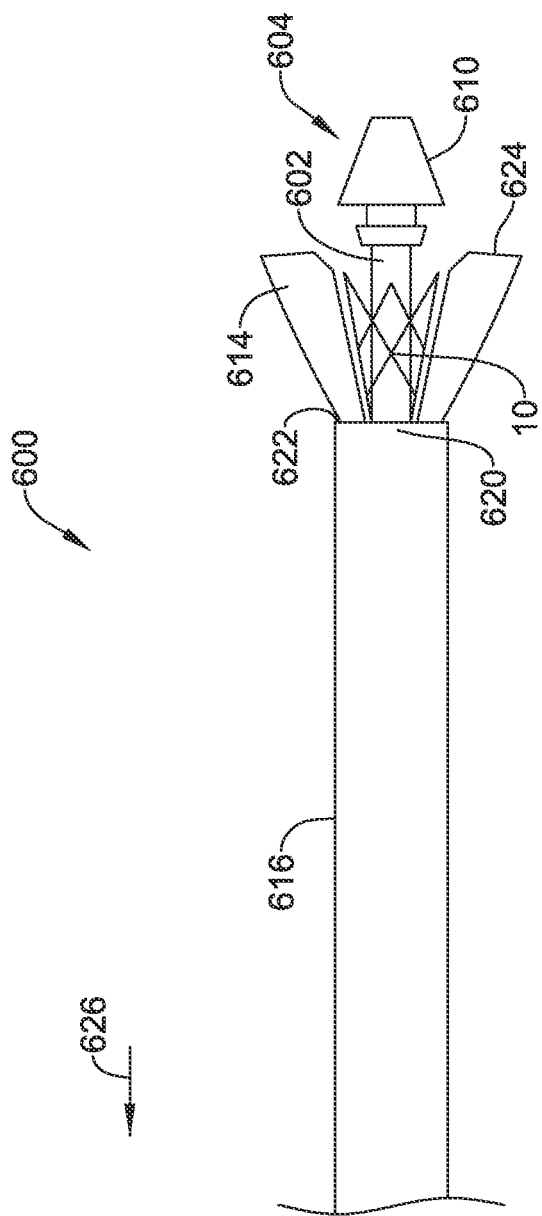
FIG. 15 illustrates another example method for delivering the illustrative implant of FIG. 1.

FIG. 15 illustrates a method of deploying the illustrative stent 10 to a body lumen using the delivery device 600 of FIG. 13. The delivery device 600 may be advanced through the desired body lumen in any suitable manner. The delivery device 600 may be advanced with or without the use of a guidewire. While FIG. 15 illustrates the outer tubular member 616 in a proximally retracted position relative to the inner tubular member 602, it is contemplated that during navigation to the target region, the distal end 622 of the outer tubular member 616 may be distal to the distal end 624 of the sheath 614. Once the stent 10 is positioned adjacent to the target region, the restraining forces maintaining the stent 10 in the radially collapsed configuration may be removed.

Once the stent 10 is adjacent to the desired location, a proximal or pulling force 626 may then be applied to the proximal end of the outer tubular member 616, as shown in FIG. 15. As the proximal end of the outer tubular member 616 is pulled or actuated, the cutting element 620 begins to move proximally and the cutting element 620 starts to cut the sheath 614, as shown in FIG. 15. In the embodiments shown in FIG. 15, the cutting element 620 is configured such that the cutting element 620 is adjacent to the distal end 16 of the stent 10 and proximal actuation thereof exposes the distal end 16 of the stent 10 first. As the biasing force of the sheath 614 is released as the cutting element 620 is proximally retracted 626, the distal end region 624 of the sheath 614 opens and the stent 10 begins to radially expand into its unbiased or deployed configuration. As the outer tubular member 616 is pulled, the cutting element 620 tears, cuts, or slices the sheath 614. In some embodiments, the sheath 614 may be perforated to facilitate cutting of the sheath 614, although this is not required. If so provided, the perforations may be generally radially aligned with the cutting element 620.

Continued proximal actuation of the outer tubular member 616 will cause more of the length of the stent 10 to be released. Proximal actuation of the proximal end of the outer tubular member 616 may continue until an entire length of the sheath 614 has been cut. It is contemplated that the clinician may continue to pull the outer tubular member 616 until the cutting element 620 has been completely removed from the body and/or the device 600 although this is not required. It is contemplated that if the sheath 614 is mechanically coupled with the outer tubular member 616, such as tethered, sutured, adhered, etc. to the outer tubular member 616, the sheath 614 may be removed with the outer tubular member 616 through continued proximal actuation of the outer tubular member 616 and/or withdrawal of the delivery device 600. In other instances, the sheath 614 may be mechanically coupled with the inner tubular member 602, such as tethered, sutured, adhered, etc. to the inner tubular member 602 proximal of the stent 10. Thus, the sheath 614 may be removed with the inner tubular member 602 during withdrawal of the delivery device 600. When in the body, the sheath 614 may retain a generally tubular configuration and may be positioned between the outer surface of the stent 10 and the body lumen. In some cases, the sheath 614 may be left in the body with the stent 10. In other embodiments, as described herein, the outer tubular member 616 may remain attached to a portion of the sheath 614 such that the sheath 614 is proximally retracted with the outer tubular member 616. In yet other embodiments, the sheath 614 may be removed using a removal tool, such as, but not limited to pinchers or clamps.

Figure 16:
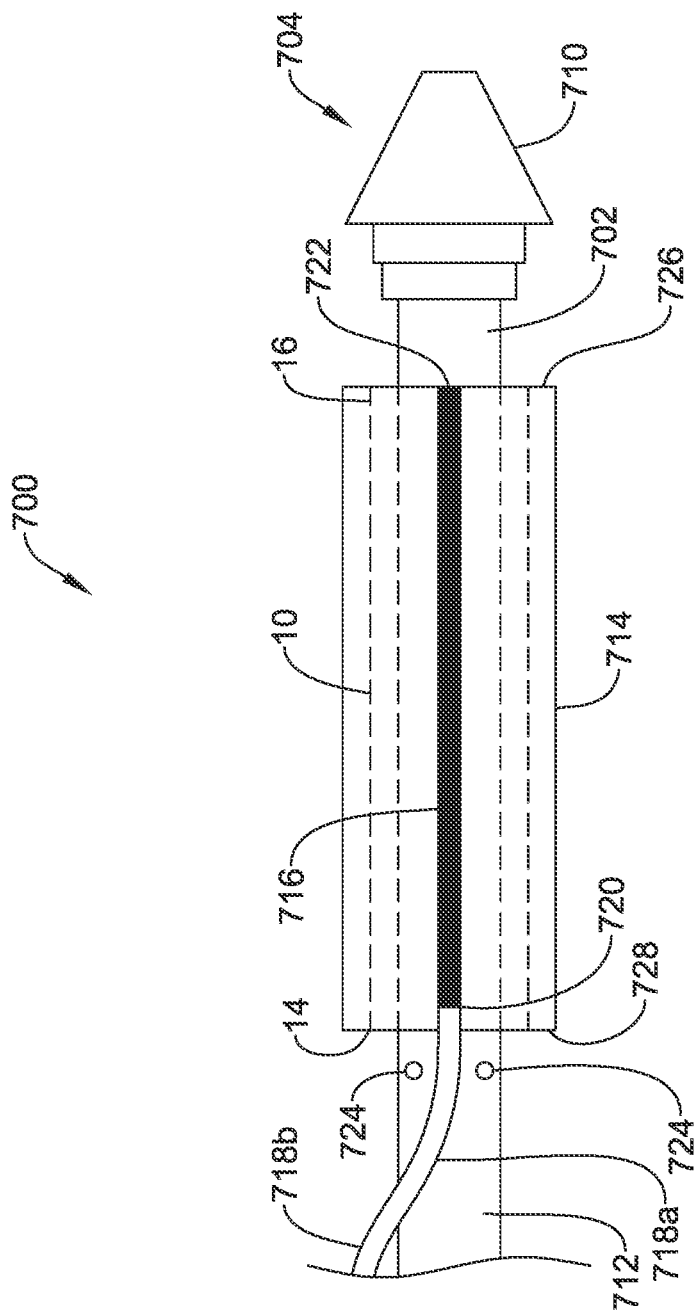
FIG. 16 is a partial side view of another illustrative delivery system for delivering the stent of FIG. 1.

FIG. 16 is a side view of another illustrative delivery system 700 for delivering a stent, such as the stent 10 described herein, to a target region. The delivery system 700 may include an elongate shaft or tubular member 702. The tubular member 702 may extend proximally from a distal end region 704 to a proximal end region (not explicitly shown) configured to remain outside of a patient's body. A hub or handle (not explicitly shown) may be coupled to the proximal end region of the tubular member 702. The tubular member 702 may further include a distal tip 710 positioned adjacent to the distal end region 704. The distal tip 710 may be configured to be atraumatic.

The tubular member 702 may include a lumen 712 extending from the distal end region 704 to the proximal end region. The lumen 712 of the tubular member 702 may also extend through the handle (if so provided). The lumen 712 of the tubular member 702 may be configured to receive a thread, pull-wire and/or guidewire, as desired.

The stent 10 may be disposed around a portion of the tubular member 702 at or adjacent to the distal end region 704 thereof. When the stent 10 is disposed over the tubular member 702, in a delivery configuration, the stent 10 may be restrained in a radially collapsed reduced diameter or delivery configuration by a sheath 714. The sheath 714 may be formed from a length of material, such as, but not limited to, a polymer or an e-spun fabric, that has been wrapped around the stent 10 prior to deployment. The sheath 714 may be wrapped about the stent 10 such that the sheath 714 surrounds and covers the length of the stent 10 during delivery. The sheath 714 may have sufficient hoop strength to retain the stent 10 in its reduced diameter state. The sheath 714 may be configured to apply a biasing force to the stent 10 which maintains the stent 10 in a collapsed or reduced diameter configuration. In some cases, the sheath 714 may include a release tab 716 which may be a strip of material that is designed to breakdown under electrical or chemical stimulus. Some illustrative materials may include, but are not limited to zinc, copper, silver, conductive polymers (which may have a low melting temperature), etc. While the release tab 716 is illustrated as extending generally parallel to a longitudinal axis of the sheath 714 this is not required. For example, the release tab 716 may be extend in a helical manner. It is further contemplated that more than one release tab 716 may be used to release the sheath 714. If so provided, two or more release tabs 716 may be uniformly spaced about the circumference of the sheath 714 or eccentrically spaced, as desired. In some cases, the release tabs 716 may extend less than an entire length of the sheath 714 or may extend along an entire length of the sheath 714, as desired.

In one example, in the case of electrical breakdown, the release tab 716 may be a strip of thin metal wire. Two electrically conductive wires 718a, 718b (collectively, 718) may be coupled to the release tab 716 to create an electrical circuit. When a high voltage is applied across the distal ends of the wires 718, the release tab 716 may breakdown (e.g., like a fuse) creating a stress concentration in the sheath 714. This may cause the sheath 714 to tear under the force of the stent and the stent 10 to release.

In another example, in the case of chemical breakdown, a release tab 716 that breaks down under certain chemical conditions (e.g., high salinity, slight acidity, etc.) could be incorporated the release tab 716. When the release tab 716 is chemically activated, the wires 718 may be omitted. Once the stent 10 is placed in its target location, an activating lavage of fluid (e.g., an acid, a base, saline, etc.) that breaks down the release tab 716 could be introduced to the area, to breakdown the release tab 716 and release the sheath 714. The fluid may be introduced in a variety of manners. In some cases, the tubular member 702 may include one or more ports 724 extending from an outer surface to an inner surface of the tubular member 102 to allow the fluid to be directed to the vicinity of the sheath 714. The tubular member 702 may include any number of ports 724 positioned at various locations along a length of the tubular member 702. For example, one or more ports 724 may be distal to the sheath 714, one or more ports 724 may be proximal to the sheath 714, one or more ports 724 may be underneath or below the sheath 714, or combinations thereof.

It is contemplated that the release tab 716 may join the longitudinally extending free ends of the sheet forming the sheath 714. While the strip of material is illustrated as extending generally parallel to the longitudinal axis of the sheath 714, the release tab 716 may have other configurations, such as, but not limited to helical, as desired. It is further contemplated that there may be more than one release tab 716. If more than one release tab 716 is provided, the release tabs 716 may be uniformly positioned about the circumference of the sheath 714 or eccentrically positioned, as desired. In some embodiments, the release tab 716 may extend a full length of the sheath 714. In other embodiments, the release tab 716 may extend less than a full length of the sheath 714. For example, a distal end 722 of the release tab 716 may extend to a distal end 726 of the sheath 714 while a proximal end 720 of the release tab 716 may be positioned distal to a proximal end 728 of the sheath 714. The reverse configuration is also contemplated in which the distal end 722 of the release tab 716 terminates proximal to the distal end 726 of the sheath 714.

The delivery device 700 may be advanced through the desired body lumen in any suitable manner. The delivery device 700 may be advanced with or without the use of a guidewire. Once the stent 10 is positioned adjacent to the target region, the restraining forces maintaining the stent 10 in the radially collapsed configuration may be removed.

Once the stent 10 is adjacent to the desired location, an electrical current may be applied to the wires 718 or an activating fluid disposed via the ports 724 depending on whether the release tab 716 is electrically or chemically activated. As the release tab 716 breaks down, the sheath 714 opens and the stent 10 begins to radially expand into its unbiased or deployed configuration. In some cases, the release tab 716 may breakdown in a proximal to distal direction, in a distal to proximal direction, or generally uniformly along the length thereof. When in the body, the sheath 714 may retain a generally tubular configuration and may be positioned between the outer surface of the stent 10 and the body lumen. In some cases, the sheath 714 may be left in the body with the stent 10. In other embodiments, the sheath 714 may be removed using a removal tool, such as, but not limited to pinchers or clamps and/or via a pulling force exerted on the electrical wires 718.

Figure 17:
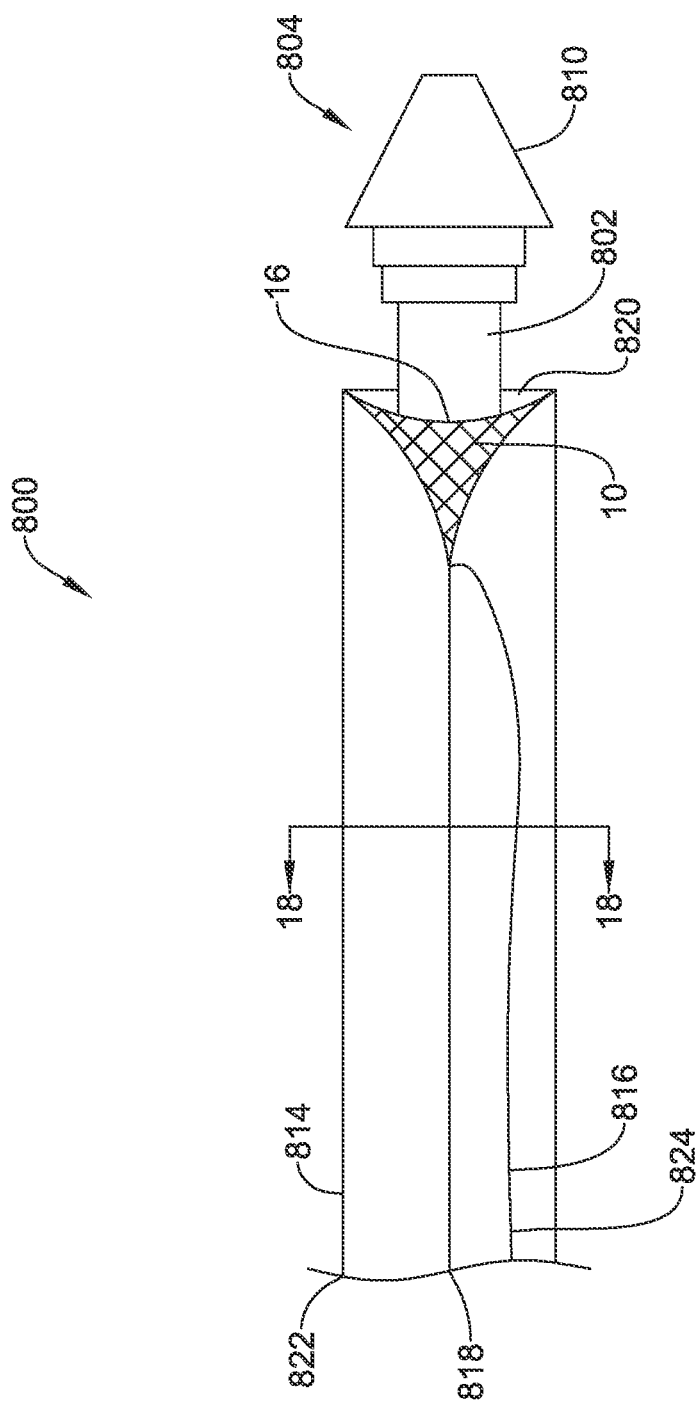
FIG. 17 is a partial side view of another illustrative delivery system for delivering the stent of FIG. 1.

FIG. 17 is a partial side view of an illustrative delivery system 800 for delivering a stent, such as the stent 10 described herein, to a target region. The delivery system 800 may include an elongate shaft or tubular member 802. The tubular member 802 may extend proximally from a distal end region 804 to a proximal end region (not explicitly shown) configured to remain outside of a patient's body. A hub or handle (not explicitly shown) may be coupled to the proximal end region of the tubular member 802. The tubular member 802 may further include a distal tip 810 positioned adjacent to the distal end region 804. The distal tip 810 may be configured to be atraumatic.

The tubular member 802 may include a lumen 812 (see, for example, FIG. 18) extending from the distal end region 804 to the proximal end region. The lumen 812 of the tubular member 802 may also extend through the handle, if so provided. The lumen 812 of the tubular member 802 may be configured to receive a thread, pull-wire and/or guidewire, as desired.

The stent 10 may be disposed around a portion of the tubular member 802 at or adjacent to the distal end region 804 thereof. When the stent 10 is disposed over the tubular member 802, in a delivery configuration, the stent 10 may be restrained in a radially collapsed reduced diameter or delivery configuration by a sheath 814. The sheath 814 may be formed from a length of material, such as, but not limited to, an e-spun fabric (e.g. a polymer that has been formed into a fabric-like sheath), that has been wrapped around the stent 10 prior to deployment. The sheath 814 may be wrapped about the stent 10 such that the sheath 814 surrounds and covers the length of the stent 10 during delivery. The sheath 814 may have sufficient hoop strength to retain the stent 10 in its reduced diameter state. In some cases, the sheath 814 may be formed from a sheet of material and sutured in a similar manner to the sheath 114 described with respect to FIG. 2. In some embodiments, the sheath 814 may be heat shrunk or otherwise formed over the stent 10.

Figure 18:
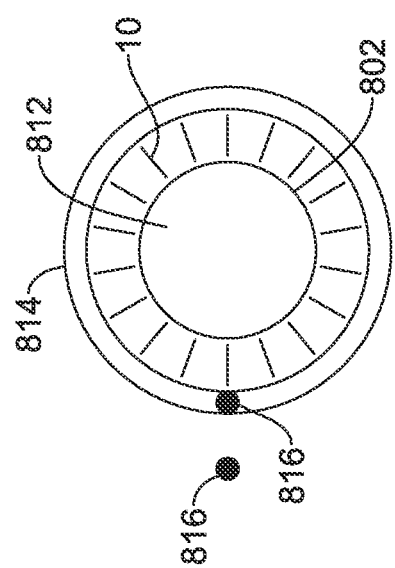
FIG. 18 is a cross-sectional view of the illustrative delivery system of FIG. 17 taken at line 18-18.

The sheath 814 may further include a tear wire or tear strip 816 embedded in a wall of the sheath 814. Referring additionally to FIG. 18 which illustrates a cross-sectional view of the delivery device 800 taken at line 18-18 in FIG. 17, the tear wire or tear strip 816 may be within a thickness of the sheath 814. In some cases, a surface or edge of the tear wire or tear strip 816 may protrude from the inner and/or outer surface of the sheath 814, and thus be exposed to the inner and/or outer surface of the sheath 814. However, this is not required. In some cases, the tear wire or tear strip 816 may be fully embedded within the wall of the sheath 814. In some embodiments, a proximal end 818 of the tear wire or tear strip 816 may be positioned adjacent to a proximal end 822 of the sheath 814. The tear wire or tear strip 816 may extend from the proximal end 822 to a distal end region 824 configured to be actuated by a user. In some cases, the distal end region 824 may be a short length of the tear wire or tear strip 816 which extends axially from the distal end 820 of the sheath 814. In other embodiments, the distal end region 824 may have a length sufficient to extend axially from the distal end 820 of the sheath 814 and fold back on itself so that it extends proximally from the distal end 820 of the sheath 814. It is contemplated that the distal end region 824 may extend proximally to a proximal end region of the delivery device 800 so that the user can directly grip the tear wire or tear strip 816 or a pull mechanism attached thereto. However, this is not required. In some cases, the distal end region 824 may be gripped and actuated with a clamp or other mechanism if the distal end region 824 is not directly grippable by the user.

Figure 19:
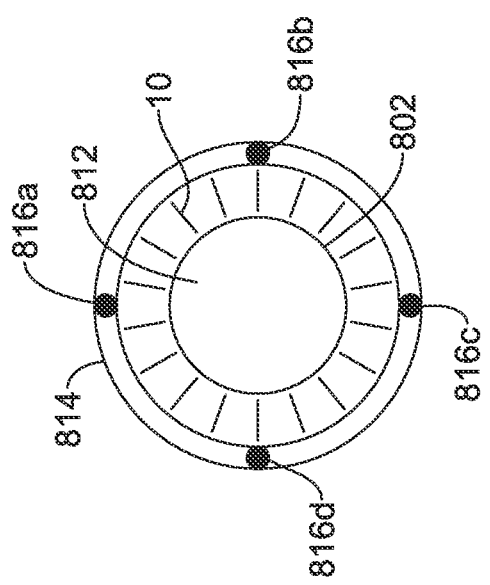
FIG. 19 is an alternative cross-sectional view of an illustrative delivery system.
Figure 20:
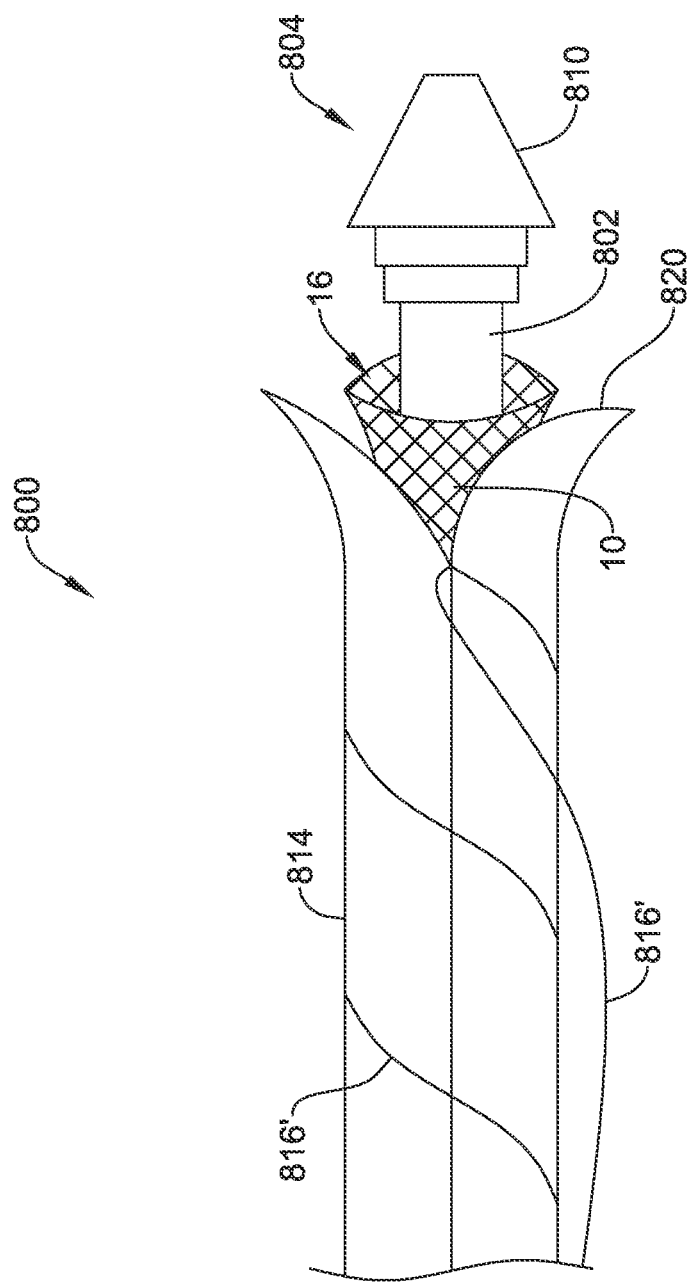
FIG. 20 is a partial side view of another illustrative delivery system for delivering the stent of FIG. 1.

While the tear wire or tear strip 816 is illustrated as extending generally parallel to a longitudinal axis of the sheath 814, in some cases, the tear wire or tear strip 816 may have a different configuration. For example, in some cases, the tear wire or tear strip 816' may have a helical configuration and extend helically around the sheath 814, as shown in FIG. 20. In some embodiments, the sheath 814 may include more than one tear wire or tear strip 816. FIG. 19 illustrates a cross-section view of the delivery device 800 including four tear wires or tear strips 816a, 816b, 816c, 816d (collectively, 816). If more than one tear wire or tear strip 816 is included, the tear wires or tear strips 816 may be uniformly spaced about a circumference of the sheath 814 or eccentrically spaced, as desired. The sheath 814 may include any number of tear wires or tear strips 816, such as one, two, three, four, or more. In some cases, when more than one tear wire or tear strip 816 is provided, the tear wires or tear strips 816 may be actuated simultaneously (through simultaneous actuation of each wire or tear strip 816 or through a common actuator) or serially (e.g., one after the other), as desired. In some cases, an embedded length of the tear wire or tear strip 816 may be less than an entire length of the sheath 814 or may be an entire length of the sheath 814, as desired.

While the tear wire or tear strip 816 is illustrated as having a proximal portion extending proximally outside of the tubular member 802, in some cases, the tubular member 802 may include an opening, skive, slot, or port adjacent the proximal end of the stent 10 to allow the tear wire or tear strip 816 to pass into the lumen 812. It is further contemplated that the tubular member 802 may include an opening, skive, slot, or port adjacent the distal end 16 of the stent 10 to allow the tear wire or tear strip 816 to pass into the lumen 812 when the tear wire or tear strip 816 is sewn in a proximal to distal direction. If so provided, the opening may extend from an outer surface to an inner surface of the tubular member 802 to allow the tear wire or tear strip 816 (or other components, as desired) to extend between the exterior of the tubular member 802 and the interior thereof.

FIGS. 17 and 20 illustrated the delivery device 800 in a partially deployed configuration. Prior to deploying the stent 10, the delivery device 800 may be advanced through the desired body lumen in any suitable manner. The delivery device 800 may be advanced with or without the use of a guidewire. Once the stent 10 is positioned adjacent to the target region, the restraining forces maintaining the stent 10 in the radially collapsed configuration may be removed.

Once the stent 10 is adjacent to the desired location, a proximal or pulling force 830 may then be applied to the distal end region 824 of the tear wire or tear strip 816. In some cases, the pulling force 830 may be applied by placing a finger inside of the pull member and pulling away from the handle. In other embodiments, a clamp or gripping tool may be advanced through the body and used to grasp the distal end region 824. As the distal end region 824 is pulled or actuated, the tear wire or tear strip 816 begins to peel away from and tear the sheath 814. As the biasing force of the sheath 814 is released as the tear wire or tear strip 816 is proximally retracted 830, the distal end region 820 of the sheath 814 opens and the stent 10 begins to radially expand into its unbiased or deployed configuration. Continued proximal actuation of the tear wire or tear strip 816 will cause more of the length of the stent 10 to be released. Proximal actuation of the tear wire or tear strip 816 may continue until the tear wire or tear strip 816 has completely released the stent 10. It is contemplated that the clinician may continue to pull the tear wire or tear strip 816 until it has been completely removed from the body and/or the device 800 although this is not required. When in the body, the sheath 814 may retain a generally tubular configuration and may be positioned between the outer surface of the stent 10 and the body lumen. In some cases, the sheath 814 may be left in the body with the stent 10. In other embodiments, the sheath 814 may be removed using a removal tool, such as, but not limited to pinchers or clamps. In yet other embodiments, the tear wire or tear strip 816 may remain attached to a portion of the sheath 814, such as a proximal end region of the sheath 814 such that the sheath 814 is proximally retracted with the tear wire or tear strip 816. For example, the sheath 814 may include a reinforced proximal portion in which the tear wire or tear strip 816 is affixed to and/or cannot sever or tear through, thus leaving the tear wire or tear strip 816 attached to the proximal end region of the sheath 814.

The stents and/or delivery devices described herein may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the stents and/or delivery devices may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of the stents and/or delivery devices in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the stents and/or delivery devices to achieve the same result.

In some embodiments, a degree of Magnetic Resonance Imaging (MM) compatibility is imparted into the stents and/or delivery devices. For example, the stents and/or delivery devices or portions thereof, may be made of a material that does not substantially distort the image and create substantial artifacts (i.e., gaps in the image). Certain ferromagnetic materials, for example, may not be suitable because they may create artifacts in an MM image. The stents and/or delivery devices or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers for the stents and/or delivery devices may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will appreciate that the different embodiments of the delivery devices described here, their mode of operation, etc., are merely representative of the environment in which the present disclosure operates. Accordingly, a variety of alternatively shaped collaborating components may also be used as a substitutive for the purpose of engaging, steering and locating the stent at a desired target site, thus, not limiting the scope of the present disclosure. Further, the disclosed implants may be adequately stretchable, extendable, and retractable, allowing for its flexible deployment. More particularly, the configurations described here may be applicable for other medical applications as well, and accordingly, a variety of other medical devices may be used in combination with the implant. Those medical devices may include biopsy forceps, scissors, lithotripters, dilators, other cautery tools, and the like.

Embodiments of the present disclosure are thus applicable to medical and/or non-medical environments. Further, certain aspects of the aforementioned embodiments may be selectively used in collaboration, or removed, during practice, without departing from the scope of the disclosed embodiments.

Those skilled in the art will recognize that the present invention may be manifested in a variety of forms other than the specific embodiments described and contemplated herein. Accordingly, departure in form and detail may be made without departing from the scope and spirit of the present disclosure as described in the appended claims.

What is claimed is:

1. A delivery system for delivering a stent to a body lumen, the system comprising:
   an outer tubular member defining a lumen and having a proximal end region and a distal end region;
   a cutting element coupled to an inner surface of the outer tubular member adjacent to the distal end region thereof, the cutting element extending radially inward from the inner surface;
   an inner tubular member defining a lumen and having a proximal end region and a distal end region, the inner tubular member slidably disposed within the lumen of the outer tubular member;
   an expandable stent disposed about an outer surface of the inner tubular member adjacent the distal end region of the inner tubular member; and
   a sheath releasably disposed over the expandable stent and configured to maintain the expandable stent in a radially collapsed configuration, the sheath having a proximal end and a distal end;
   wherein the cutting element is configured to cut an entire length of the sheath, from the proximal end of the sheath to the distal end of the sheath, upon proximal retraction of the outer tubular member while remaining radially spaced from the expandable stent.

2. The delivery system of claim 1, wherein the cutting element comprises a blade.

3. The delivery system of claim 1, wherein the cutting element comprises a saw tooth blade.

4. The delivery system of claim 1, wherein the cutting element comprises a pair of blades secured together to form a V shaped cutting surface.

5. The delivery system of claim 1, wherein the cutting element comprises two or more cutting elements uniformly positioned about a circumference of the inner surface of the outer tubular member.

6. The delivery system of claim 1, wherein the cutting element comprises two or more cutting elements eccentrically positioned about a circumference of the inner surface of the outer tubular member.

7. The delivery system of claim 1, wherein an inner diameter of the outer tubular member is greater than an outer diameter of the sheath.

8. The delivery system of claim 1, wherein the sheath comprises a plurality of perforations.

9. The delivery system of claim 8, wherein the plurality of perforations are radially aligned with the cutting element.

10. The delivery system of claim 1, wherein upon proximal retraction of the outer tubular member, the sheath is released from the stent.

11. The delivery system of claim 1, wherein after the sheath is cut through proximal retraction of the outer tubular member, the sheath is configured to be removable.

12. A delivery system for delivering a stent to a body lumen, the system comprising:
   an inner member having a proximal end region and a distal end region;
   an expandable stent disposed about an outer surface of the inner member adjacent the distal end region of the inner member;
   a sheath releasably disposed over the expandable stent and configured to maintain the expandable stent in a radially collapsed configuration;
   an outer tubular member defining a lumen, wherein the inner member, the expandable stent, and the sheath are disposed within the lumen of the outer tubular member;
   wherein the sheath is tethered to either the inner or outer tubular member with a tether; and
   a cutting element extending into the lumen of the outer tubular member adjacent to the distal end region thereof, the cutting element moveable with the outer tubular member;
   wherein the cutting element is configured to cut the sheath upon proximal retraction of the outer tubular member relative to the sheath.

13. The delivery system of claim 12, wherein the sheath comprises a plurality of perforations.

14. The delivery system of claim 13, wherein the plurality of perforations are radially aligned with the cutting element.

15. The delivery system of claim 12, wherein upon proximal retraction of the outer tubular member, the sheath is released from the stent.

16. The delivery system of claim 12, wherein after the sheath is cut through proximal retraction of the outer tubular member, the sheath is configured to be removable.

17. A delivery system for delivering a stent to a body lumen, the system comprising:
   an inner member having a proximal end region, a distal end region, and a longitudinal axis extending therebetween;
   an expandable stent disposed about an outer surface of the inner member adjacent the distal end region of the inner member;

a sheath releasably disposed over the expandable stent and constraining the expandable stent in a radially collapsed configuration;

an outer tubular member surrounding the sheath and longitudinally moveable relative to the sheath and the expandable stent; and a cutting element fixed to the outer tubular member adjacent to the distal end region thereof and moveable with the outer tubular member, the cutting element extending from the outer tubular member toward the longitudinal axis of the inner member;

the outer tubular member proximally retractable from a first position to a second position;

wherein the cutting element is configured to cut along an entire length of the sheath, from a distalmost extent of the sheath to a proximalmost extent of the sheath, upon proximal retraction of the outer tubular member relative to the sheath to the second position.

18. The delivery system of claim 17, wherein upon proximal retraction of the outer tubular member, the sheath is released from the stent.

19. The delivery system of claim 17, wherein the sheath comprises a plurality of perforations, and wherein the plurality of perforations are radially aligned with the cutting element.

20. The delivery system of claim 17, wherein the sheath is tethered to either the inner or outer tubular member with a tether.

* * * * *